(12) United States Patent
Atsumi et al.

(10) Patent No.: US 9,969,699 B2
(45) Date of Patent: May 15, 2018

(54) CANCER CELL GROWTH INHIBITOR, ANTICANCER AGENT, AND METHOD FOR SCREENING SAME, AS WELL AS NOVEL COMPOUND

(71) Applicants: Microbial Chemistry Research Foundation, Tokyo (JP); Gakubunkan, Tokyo (JP); Kyoko Nomoto, Tokyo (JP)

(72) Inventors: Sonoko Atsumi, Tokyo (JP); Masabumi Shibuya, Gunma (JP); Shun-ichi Ohba, Tokyo (JP); Tomoyuki Kimura, Tokyo (JP); Yoshihiko Kobayashi, Tokyo (JP); Hayamitsu Adachi, Tokyo (JP); Chisato Nosaka, Tokyo (JP); Akio Nomoto, Tokyo (JP)

(73) Assignees: Microbial Chemistry Research Foundation (JP); GAKUBUNKAN (JP)

( * ) Notice: Subject to any disclaimer, the term of this patent is extended or adjusted under 35 U.S.C. 154(b) by 0 days. days.

(21) Appl. No.: 15/511,859

(22) PCT Filed: Sep. 7, 2015

(86) PCT No.: PCT/JP2015/075330
§ 371 (c)(1),
(2) Date: Mar. 16, 2017

(87) PCT Pub. No.: WO2016/052081
PCT Pub. Date: Apr. 7, 2016

(65) Prior Publication Data
US 2017/0291879 A1    Oct. 12, 2017

(30) Foreign Application Priority Data
Sep. 30, 2014   (JP) .................. 2014-200736

(51) Int. Cl.
*C07D 241/44* (2006.01)
*G01N 33/50* (2006.01)

(52) U.S. Cl.
CPC ....... *C07D 241/44* (2013.01); *G01N 33/5011* (2013.01); *G01N 2333/71* (2013.01)

(58) Field of Classification Search
CPC ............. C07D 241/44; G01N 33/5011; G01N 2333/71
USPC ......................................................... 514/249
See application file for complete search history.

(56) References Cited

PUBLICATIONS

Cancer [online], [retrieved on Jul. 6, 2007] Retrieved from the Internet, URL: http://www.nlm.nih.gov/medlineplus/cancer.html.*
Lala et al., Role of nitric oxide in tumor progression: Lessons from experimental tumors, Cancer and Metastasis Reviews (1998), 17, 91-106.*
Golub et al., Molecular Classification of Cancer: Class Discovery and Class Prediction by Gene Expression Monitoring, Science (1999), vol. 286, 531-537.*
Schmidt et al., "Expression of an Oncogenic Mutant EGF Receptor Markedly Increases the Sensitivity of Cells to an EGF-Receptor-Specific Antibody-Toxin," Int. J. Cancer, vol. 75, pp. 878-886 (1998).
Gauvin et al., "Isoform-Selective Chemical Inhibition of mDia-Mediated Actin Assembly," Biochemistry, vol. 48, pp. 9327-9329 (2009).
Weiwer et al., "A Potent and Selective Quinoxalinone-Based STK33 Inhibitor Does Not Show Synthetic Lethality in KRAS-Dependent Cells," ACS Med. Chem. Lett., vol. 3, pp. 1034-1038 (2012).

* cited by examiner

*Primary Examiner* — Kristin Vajda
(74) *Attorney, Agent, or Firm* — Carmody Torrance Sandak & Hennessey LLP

(57) ABSTRACT

A cancer cell proliferation inhibitor including at least one selected from compounds represented by Structural Formulae (1) to (8), wherein the cancer cell is at least one of a cancer cell overexpressing a wild-type epidermal growth factor receptor and a cancer cell expressing an epidermal growth factor receptor mutant vIII.

9 Claims, 9 Drawing Sheets

Negative control group

Compound represented by Structural Formula (1) administration group

Positive control group

Negative control group

Compound represented by Structural Formula (1) administration group

Positive control group

CANCER CELL GROWTH INHIBITOR, ANTICANCER AGENT, AND METHOD FOR SCREENING SAME, AS WELL AS NOVEL COMPOUND

TECHNICAL FIELD

The present invention relates to a cancer cell proliferation inhibitor that is capable of inhibiting proliferation of at least one of a cancer cell overexpressing a wild-type epidermal growth factor receptor and a cancer cell expressing an epidermal growth factor receptor mutant vIII; an anti-cancer agent that includes the cancer cell proliferation inhibitor; a screening method of the cancer cell proliferation inhibitor or the anti-cancer agent; and a novel compound suitable for the cancer cell proliferation inhibitor and the anti-cancer agent.

BACKGROUND ART

Epidermal growth factor receptors (hereinafter may be referred to as "EGFRs") are receptor tyrosine kinases to which ligands such as epidermal growth factors (hereinafter may be referred to as "EGFs") bind to activate intramembrane kinases to thereby lead to signal transduction. It has been known that although the EGFRs are also present in normal tissues, they are frequently mutated or amplified in cancer tissues to cause oncogenesis.

For example, EGFR genes in genomes are mutated or amplified in about 60% of cancer tissues in patients with glioblastoma, a highly malignant cancer. Moreover, epidermal growth factor receptor mutant vIII (hereinafter may be referred to as "EGFR vIII") proteins, in which exons 2 to 7 are deleted, are overexpressed in half of the about 60% of cancer tissues. The EGFR vIII proteins are deficient in ligand-binding sites and are constitutively activated without ligands. The EGFR vIII proteins are expressed only in cancer tissues and have been believed to be involved in malignant transformation of cancer.

For example, AG1478, Gefitinib, and Erlotinib, which are EGFR kinase inhibitors, are promising therapeutic drugs for cancers in which mutation or amplification of the EGFRs are involved.

However, they have unsatisfactory anti-cancer effects. Therefore, keen demand has arisen for developing a more effective anti-cancer agent and a screening method for screening such an anti-cancer agent.

Note that, a compound represented by Structural Formula (1) below (hereinafter may be referred to as "Ertredin") has been reported to inhibit mDia-mediated actin assembly in vitro (see, e.g., NPL 1). However, the compound has not been known to exhibit physiological activities such as kinase inhibiting activities.

CITATION LIST

Non-Patent Literature

NPL 1: Gauvin T J1, Fukui J, Peterson J R, Higgs H N, Isoform-selective chemical inhibition of mDia-mediated actin assembly, Biochemistry, 48 (40), 9327-9329 (2009)

SUMMARY OF INVENTION

Technical Problem

The present invention has been made in view of the foregoing related art, and aims to achieve the following object. That is, the present invention has an object to provide a low-toxic cancer cell proliferation inhibitor that has an excellent proliferation inhibiting activity against at least one of a cancer cell overexpressing a wild-type epidermal growth factor receptor and a cancer cell expressing an epidermal growth factor receptor mutant vIII; an anti-cancer agent that has an excellent anti-tumor activity; a screening method that is capable of efficiently screening at least one of the cancer cell proliferation inhibitor and the anti-cancer agent; and a novel compound suitable for the cancer cell proliferation inhibitor and the anti-cancer agent.

Solution to Problem

Means for solving the above problems are as follows.

<1> a Cancer Cell Proliferation Inhibitor Including at least one selected from compounds represented by Structural Formulae (1) to (8) below, wherein the cancer cell is at least one of a cancer cell overexpressing a wild-type epidermal growth factor receptor and a cancer cell expressing an epidermal growth factor receptor mutant vIII:

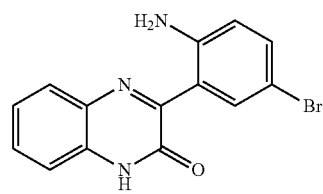

Structural Formula (1)

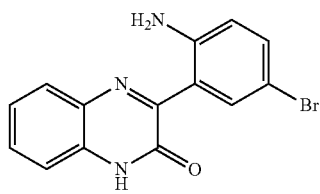

Structural Formula (1)

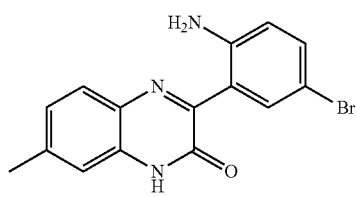

Structural Formula (2)

-continued

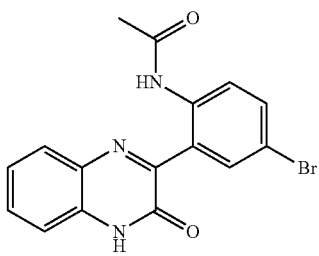
Structural Formula (3)

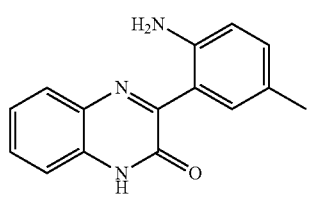
Structural Formula (4)

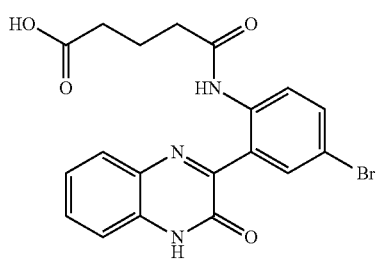
Structural Formula (5)

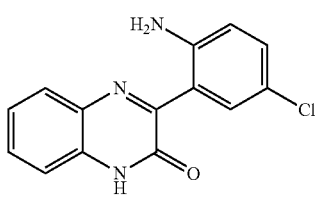
Structural Formula (6)

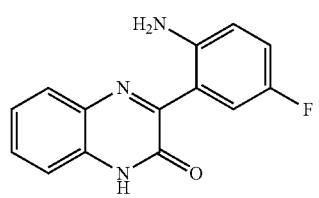
Structural Formula (7)

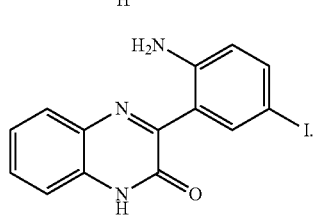
Structural Formula (8)

<2> An anti-cancer agent including
the cancer cell proliferation inhibitor according to <1>.

<3> A method for screening at least one of a cancer cell proliferation inhibitor and an anti-cancer agent, the method including:
culturing a NIH3T3 cell expressing an epidermal growth factor receptor mutant vIII in a medium including a test substance under an environment without an adhesion scaffold;
culturing a NIH3T3 cell in a medium including the test substance under an environment with an adhesion scaffold; and
evaluating the test substance as having an activity as at least one of the cancer cell proliferation inhibitor and the anti-cancer agent when the test substance does not inhibit proliferation of the NIH3T3 cell, but inhibits proliferation of the NIH3T3 cell expressing an epidermal growth factor receptor mutant vIII.

<4> A method for preventing or treating a cancer, the method including
administering the anti-cancer agent according to <2> to an individual.

<5> A compound represented by Structural Formula (8) below:

Structural Formula (8)

<6> A compound-including composition including the compound according to <5>.

Advantageous Effects of Invention

The present invention is capable of achieving the above objects and providing a low-toxic cancer cell proliferation inhibitor that has an excellent proliferation inhibiting activity against at least one of a cancer cell overexpressing wild-type epidermal growth factor receptor and a cancer cell expressing an epidermal growth factor receptor mutant vIII; an anti-cancer agent that has an excellent anti-tumor activity; a screening method that is capable of efficiently screening at least one of the cancer cell proliferation inhibitor and the anti-cancer agent; and a novel compound suitable for the cancer cell proliferation inhibitor and the anti-cancer agent.

BRIEF DESCRIPTION OF DRAWINGS

FIG. 4-1 is a graph illustrating results of an acute toxicity test in Test Example 4-1.

FIG. 4-2 is a graph illustrating results of an acute toxicity test in Test Example 4-2.

FIG. 4-3 is a graph illustrating results of an acute toxicity test in Test Example 4-3.

FIG. 5-1 is a graph illustrating measurement results of tumor volumes in Test Example 5-1.

FIG. 5-2 is a graph illustrating measurement results of tumor weights in Test Example 5-1.

FIG. 5-3 is an image of tumors removed in Test Example 5-1.

FIG. 5-4 is a graph illustrating measurement results of mouse body weights in Test Example 5-1.

FIG. 6-1 is a graph illustrating measurement results of tumor volumes in Test Example 5-2.

FIG. 6-2 is a graph illustrating measurement results of tumor weights in Test Example 5-2.

FIG. 6-3 is an image of tumors removed in Test Example 5-2.

FIG. 6-4 is a graph illustrating measurement results of mouse body weights in Test Example 5-2.

FIG. 7-1 is a graph illustrating results of an acute toxicity test in Test Example 6-1.

FIG. 7-2 is a graph illustrating results of an acute toxicity test in Test Example 6-2.

FIG. 8-1 is a graph illustrating measurement results of tumor weights in Test Example 7.

FIG. 8-2 is a graph illustrating measurement results of mouse body weights in Test Example 7.

DESCRIPTION OF EMBODIMENTS (Novel Compound)

Figure 1:
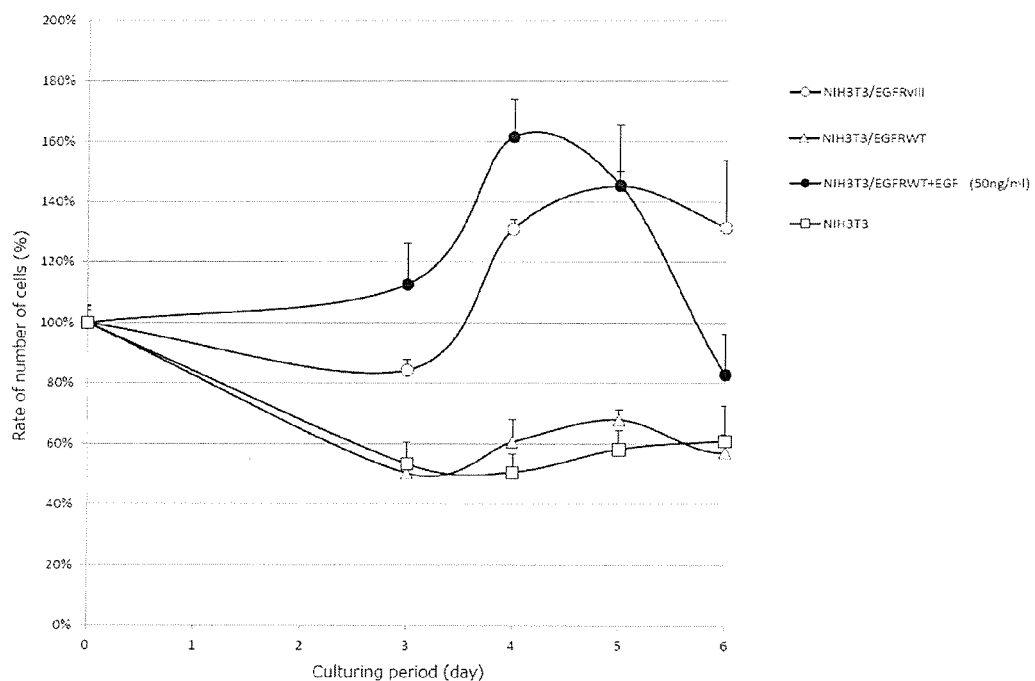
FIG. 1 is a graph illustrating results of cell culture in Test Example 1.

A compound of the present invention is a compound represented by Structural Formula (8) below, (3-(2-amino-5-iodophenyl)-2(1H)-quinoxalinone), which is a novel compound found by the present inventors.

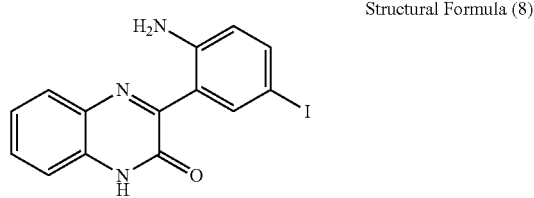

Structural Formula (8)

<Physico-Chemical Property>

The compound represented by Structural Formula (8) was measured by $^1$H NMR, $^{13}$C-NMR, COSY, HMQC, HMBC, and HRMS. The results are described below.

$^1$H NMR (600 MHz, DMSO-$d_6$): δ 6.64 (2H, br. s, NH$_2$), 6.65, (1H, d, J=4.0 Hz, H-3'), 7.28 (1H, dt, J=4.0, 4.0 and 0.5 Hz, H-6), 7.30 (1H, dd, J=4.0 and 0.5 Hz, H-8), 7.38 (1H, dd, J=4.0 and 1.0 Hz, H-4'), 7.49 (1H, dt, J=4.0, 4.0 and 0.5 Hz, H-7), 7.79 (1H, dd, J=4.0 and 0.5 Hz, H-5), 8.41 (1H, d, J=1.5 Hz, H-6') and 12.50 (1H, bs, NH).

$^{13}$C NMR (150.9 MHz, DMSO-$d_6$): δ 74.75 (C-5'), 115.41 (C-8), 118.68 (C-3'), 120.04 (C-1'), 123.03 (C-6), 128.09 (C-5), 129.79 (C-7), 131.30 (C-4a and -8a), 138.37 (C-4'), 138.99 (C-6'), 148.40 (C-2'), 154.16 (C-3) and 155.06 (C-2).

HRMS m/z Found 363.9944 (M+H)+, Calcd. 363.9941.

Whether a compound has a structure represented by Structural Formula (8) may be determined by appropriately selected various analysis methods. Examples thereof include mass spectrometry, ultraviolet spectroscopy, infrared spectroscopy, proton nuclear magnetic resonance spectrometry, and $^{13}$C nuclear magnetic resonance spectrometry. Note that, measurements obtained by the above analysis methods may have some errors, but those skilled in the art are capable of easily identifying whether the compound has the structure represented by Structural Formula (8).

The compound may be a salt of the compound represented by Structural Formula (8).

The salt is not particularly limited and may be appropriately selected depending on the intended purpose, so long as it is a pharmacologically acceptable salt. Examples thereof include organic salts such as acetates and citrates, hydrochlorides, and carbonates.

The compound represented by Structural Formula (8) may be a tautomer thereof.

A method for producing the compound represented by Structural Formula (8) is not particularly limited and may be appropriately selected depending on the intended purpose. For example, the compound may be produced by chemical synthesis.

The compound represented by Structural Formula (8) may be chemically synthesized, for example, with reference to "Synthetic Communications 2011, 41, 1650."

Specifically, acetic acid (1.5 mL) is added to 5-iodoisatin (81.9 mg, 0.30 mmol) and 1,2-phenylenediamine (32.4 mg, 0.30 mmol), followed by stirring at room temperature for 2 days. After reaction, the resultant reaction product is azeotroped with toluene. The resultant orange solid is purified by preparative thin-layer chromatography [hexane:ethyl acetate=1:1 (volume ratio)]. Thus, the compound represented by Structural Formula (8) is capable of being obtained as an orange solid.

The compound represented by Structural Formula (8) has an excellent cancer cell proliferation inhibiting activity and an excellent anti-tumor activity and has low toxicity. Therefore, the compound is capable of being suitably used as, for example, a compound-including composition, a cancer cell proliferation inhibitor, or an anti-tumor agent of the present invention as described below.

(Compound-Including Composition)

A compound-including composition of the present invention at least includes the compound represented by Structural Formula (8); and, if necessary, further includes other components.

An amount of the compound represented by Structural Formula (8) included in the compound-including composition is not particularly limited and may be appropriately selected depending on the intended purpose. The compound-including composition is the compound represented by Structural Formula (8) itself.

<Other Components>

The other components are not particularly limited and may be appropriately selected depending on the intended purpose. Examples thereof include pharmacologically acceptable carriers and at least one of compounds represented by the Structural Formulae (1) to (7). These may be used alone or in combination.

Examples of the pharmacologically acceptable carriers include additives, auxiliary agents, and water.

The additives or auxiliary agents are not particularly limited and may be appropriately selected depending on the intended purpose. Examples thereof include disinfectants, preservatives, caking agents, thickeners, adhesive agents, binding agents, colorants, stabilizers, pH adjusters, buffers, isotonizing agents, solvents, antioxidants, anti-UV agents, agents for preventing crystal deposition, defoaming agents, agents for improving physical properties, and antiseptic agents.

The disinfectants are not particularly limited and may be appropriately selected depending on the intended purpose. Examples thereof include cationic surfactants such as benzalkonium chloride, benzethonium chloride, and cetylpyridinium chloride.

The preservatives are not particularly limited and may be appropriately selected depending on the intended purpose. Examples thereof include paraoxybenzoic acid esters, chlorobutanol, and cresol.

The caking agents, thickeners or adhesive agents are not particularly limited and may be appropriately selected depending on the intended purpose. Examples thereof include starch, dextrin, cellulose, methyl cellulose, ethyl cellulose, carboxymethyl cellulose, hydroxyethyl cellulose, hydroxypropyl cellulose, hydroxypropyl methylcellulose, carboxymethyl starch, pullulan, sodium alginate, ammonium alginate, propyleneglycol alginate, guar gum, locust bean gum, gum Arabic, xanthane gum, gelatin, casein, polyvinyl alcohol, polyethylene oxide, polyethylene glycol, ethylene/propylene block polymers, sodium polyacrylates, and polyvinylpyrrolidone.

The binding agents are not particularly limited and may be appropriately selected depending on the intended purpose. Examples thereof include water, ethanol, propanol, simple syrup, glucose liquid, starch liquid, gelatin liquid, carboxymethyl cellulose, hydroxypropyl cellulose, hydroxypropyl starch, methyl cellulose, ethyl cellulose, shellac, calcium phosphate, and polyvinylpyrrolidone.

The colorants are not particularly limited and may be appropriately selected depending on the intended purpose. Examples thereof include titanium oxide and iron oxide.

The stabilizers are not particularly limited and may be appropriately selected depending on the intended purpose. Examples thereof include tragacanth, gum Arabic, gelatin, sodium pyrosulfite, ethylenediamine tetraacetate (EDTA), thioglycolic acid, and thiolactic acid.

The pH adjusters or the buffers are not particularly limited and may be appropriately selected depending on the intended purpose. Examples thereof include sodium citrate, sodium acetate, and sodium phosphate.

The isotonizing agents are not particularly limited and may be appropriately selected depending on the intended purpose. Examples thereof include sodium chloride and glucose.

An amount of the other components included in the compound-including composition is not particularly limited and may be appropriately selected depending on the intended purpose, so long as they do not impair effects of the compound represented by Structural Formula (8).

<Use>

The compound-including composition includes the compound represented by Structural Formula (8) and therefore has an excellent cancer cell proliferation inhibiting activity and an excellent anti-tumor activity and has low toxicity. Therefore, the compound-including composition is capable of being suitably used as, for example, a cancer cell proliferation inhibitor or an anti-tumor agent of the present invention as described below.

The compound-including composition may be used alone or in combination with a pharmaceutical composition including, as an active component, another component. The compound-including composition may also be used in a state of being formulated into a pharmaceutical composition including, as an active component, another component.

(Cancer Cell Proliferation Inhibitor)

A cancer cell proliferation inhibitor of the present invention includes at least one selected from compounds represented by Structural Formulae (1) to (8) below; and, if necessary, further includes other components:

Structural Formula (1)

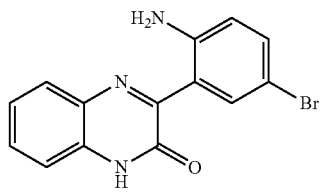

Structural Formula (2)

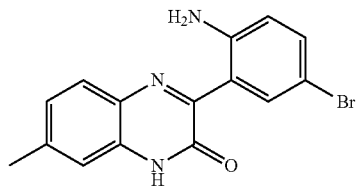

Structural Formula (3)

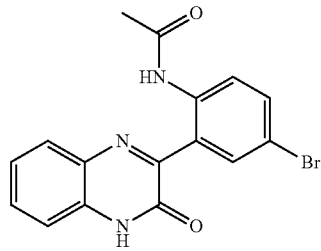

Structural Formula (4)

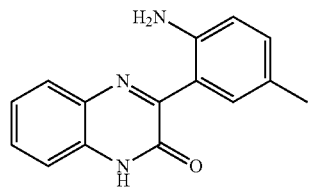

Structural Formula (5)

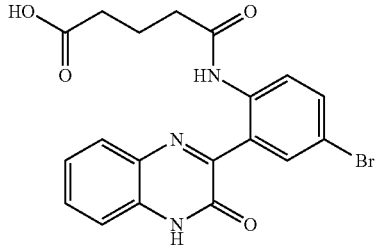

Structural Formula (6)

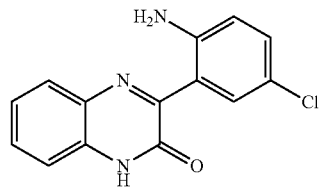

Structural Formula (7)

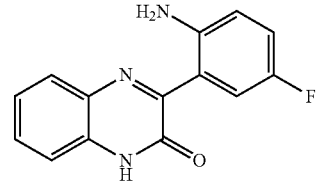

Structural Formula (8)

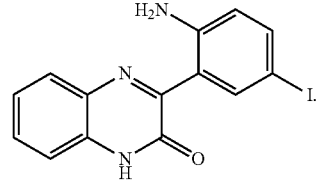

The cancer cell proliferation inhibitor of the present invention inhibits proliferation of at least one of a cancer cell overexpressing a wild-type epidermal growth factor receptor and a cancer cell expressing an epidermal growth factor receptor mutant vIII.

As used herein, the expression "overexpressing a wild-type epidermal growth factor receptor" means that the wild-type epidermal growth factor receptor is more highly expressed than in a normal cell. The overexpressing may be overexpressing of genes, proteins, or both thereof.

Specific examples of the cancer cell overexpressing a wild-type epidermal growth factor receptor include glioblastoma cells, head and neck cancer cells, breast cancer cells, renal cancer cells, cervical cancer cells, uterine cancer cells, esophageal cancer cells, pancreas cancer cells, non-small cell lung cancer cells, prostatic cancer cells, colon cancer cells, ovarian cancer cells, bladder cancer cells, stomach cancer cells, and thyroid cancer cells.

Specific examples of the cancer cell expressing an epidermal growth factor receptor mutant vIII include glioblastoma cells, non-small cell lung cancer cells, breast cancer cells, and thyroid cancer cells.

The cancer cell proliferation inhibitor is capable of suitably inhibiting proliferation of glioblastoma cells.

<Compounds Represented by Structural Formulae (1) to (8)>

The compounds represented by Structural Formulae (1) to (8) may be used alone or in combination.

Among the compounds represented by Structural Formulae (1) to (8), at least one selected from the compound represented by Structural Formula (1), the compound represented by Structural Formula (6), and the compound represented by Structural Formula (8) are preferable from the viewpoint of an excellent cancer cell proliferation inhibiting activity.

The compounds represented by Structural Formulae (1) to (8) may be salts thereof.

The salts are not particularly limited and may be appropriately selected depending on the intended purpose. Examples thereof include organic salts such as acetates and citrates, hydrochlorides, and carbonates.

The compounds represented by Structural Formulae (1) to (7) are known compounds.

The compounds represented by Structural Formulae (1) to (7) may be commercially available products or chemically synthesized.

A method for chemically synthesizing the compounds is not particularly limited and may be appropriately selected depending on the intended purpose. For example, the compounds may be synthesized according to "Synthetic Communications 2011, 41, 1650."

The compound represented by Structural Formula (8) may be produced according to the chemical synthesis method described under the section entitled "Novel compound."

An amount of the compounds represented by Structural Formulae (1) to (8) included in the cancer cell proliferation inhibitor is not particularly limited and may be appropriately selected depending on the intended purpose. The cancer cell proliferation inhibitor may consist of at least one of the compounds represented by Structural Formulae (1) to (8).

<Other Components>

Other components in the cancer cell proliferation inhibitor are not particularly limited and may be appropriately selected depending on the intended purpose. Examples thereof include pharmacologically acceptable carriers. These may be used alone or in combination.

The pharmacologically acceptable carriers may be the same as those described under the section entitled "Other components" for the compound-including composition.

An amount of the other components included in the cancer cell proliferation inhibitor is not particularly limited and may be appropriately selected depending on the intended purpose.

<Use>

The cancer cell proliferation inhibitor may be suitably used as an active component of an anti-cancer agent described below.

Note that, the cancer cell proliferation inhibitor may be used alone or in combination with a pharmaceutical including, as an active component, another component. The cancer cell proliferation inhibitor may also be used in a state of being formulated into a pharmaceutical including, as an active component, another component.

The cancer cell proliferation inhibitor is capable of inhibiting proliferation of a cancer cell. Therefore, the present invention also relates to a method for inhibiting proliferation of a cancer cell.

<Dosage Form>

A dosage form of the cancer cell proliferation inhibitor is not particularly limited and may be appropriately selected depending on the intended purpose. Examples thereof include solid dosage forms, semi-solid dosage forms, and liquid dosage forms. The cancer cell proliferation inhibitor in the form of any of the above dosage forms is capable of being produced according to a routine method.

—Solid Dosage Forms—

The solid dosage forms are not particularly limited and may be appropriately selected depending on the intended purpose. When the solid dosage forms are internally used, examples of the solid dosage forms include tablets, chewable tablets, foaming tablets, orally-disintegrating tablets, troches, drops, hard capsules, soft capsules, granules, powder, pills, dry syrups, and infusions.

When the solid dosage forms are externally used, examples of the solid dosage forms include suppositories, cataplasms, and plasters.

—Semi-Solid Dosage Forms—

The semi-solid dosage forms are not particularly limited and may be appropriately selected depending on the intended purpose. When the semi-solid dosage forms are internally used, examples of the semi-solid dosage forms include electuaries, chewing gums, whips, and jellies.

When the semi-solid dosage forms are externally used, examples of the semi-solid dosage forms include ointments, creams, mousses, inhalers, and nasal gels.

—Liquid Dosage Forms—

The liquid dosage forms are not particularly limited and may be appropriately selected depending on the intended purpose. When the liquid dosage forms are internally used, examples of the liquid dosage forms include syrups, drinks, suspensions, and spirits.

When the liquid dosage forms are externally used, examples of the liquid dosage forms include solutions, eye drops, aerosol, and sprays.

<Administration>

An administration method, administration dose, administration timing, and administration target of the cancer cell proliferation inhibitor are not particularly limited and may be appropriately selected depending on the intended purpose.

Examples of the administration method include parenteral administration methods and oral administration methods such as local administration methods, enteral administration methods, intrathecal administration methods, intravenous administration methods, and intraperitoneal administration methods.

The administration dose is not particularly limited and may be appropriately selected considering various factors such as age, body weight, physical constitution, or symptom of an administration target individual, and the presence or absence of administration of a pharmaceutical or drug including, as an active component, another component.

The administration target is not particularly limited and may be appropriately selected depending on the intended purpose. Examples thereof include human, monkey, pig, bovine, sheep, goat, dog, cat, mouse, rat, and birds. Among them, human is suitable.

(Anti-Cancer Agent)

An anti-cancer agent of the present invention at least includes the cancer cell proliferation inhibitor; and, if necessary, further includes other components.

<Cancer Cell Proliferation Inhibitor>

The cancer cell proliferation inhibitor is the cancer cell proliferation inhibitor of the present invention described above.

The cancer cell proliferation inhibitor preferably includes at least one selected from the compound represented by Structural Formula (1), the compound represented by Structural Formula (6), and the compound represented by Structural Formula (8) from the viewpoint of an excellent tumor proliferation inhibiting activity.

An amount of the cancer cell proliferation inhibitor included in the anti-cancer agent is not particularly limited and may be appropriately selected depending on the intended purpose. The anti-cancer agent may consist of the cancer cell proliferation inhibitor.

<Other Components>

Other components in the anti-cancer agent are not particularly limited and may be appropriately selected depending on the intended purpose. Examples thereof include pharmacologically acceptable carriers. These may be used alone or in combination.

The pharmacologically acceptable carriers may be the same as those described under the section entitled "Other components" for the compound-including composition.

An amount of the other components included in the anti-cancer agent is not particularly limited and may be appropriately selected depending on the intended purpose.

<Use>

The anti-cancer agent includes at least one of the compounds represented by Structural Formulae (1) to (8) and therefore has an excellent anti-cancer effect and is highly safe. Therefore, the anti-cancer agent is capable of being suitably used as, for example, a prophylactic agent or therapeutic agent for at least one of the cancer cell overexpressing a wild-type epidermal growth factor receptor and the cancer cell expressing an epidermal growth factor receptor mutant vIII. Among them, the anti-cancer agent may be particularly suitably used for glioblastoma.

Note that, the anti-cancer agent may be used alone or in combination with a pharmaceutical including, as an active component, another component. The anti-cancer agent may also be used in a state of being formulated into a pharmaceutical including, as an active component, another component.

The anti-cancer agent of the present invention is capable of specifically inhibiting proliferation of a cancer cell without inhibiting proliferation of a normal cell, as demonstrated in Test Examples described below.

The anti-cancer agent includes at least one of the compounds represented by Structural Formulae (1) to (8). Therefore, the anti-cancer agent is capable of being administered to an individual to prevent cancer from developing in the individual or treat the individual suffering from cancer. Therefore, the present invention also relates to a method for preventing or treating cancer including administering the anti-cancer agent to an individual.

<Dosage Form>

A dosage form of the anti-cancer agent is not particularly limited and may be appropriately selected depending on the intended purpose. For example, the dosage form may be the same as those described under the section entitled "Dosage form" for the cancer cell proliferation inhibitor.

<Administration>

An administration method, administration dose, administration timing, and administration target of the anti-cancer agent are not particularly limited and may be appropriately selected depending on the intended purpose. For example, they may be the same as those described under the section entitled "Administration" for the cancer cell proliferation inhibitor.

(Screening Method)

A screening method of the present invention is a method for screening at least one of a cancer cell proliferation inhibitor and an anti-cancer agent.

The screening method at least includes a 3D cell culture step, a 2D cell culture step, and an evaluation step; and, if necessary, further includes other steps.

The screening method of the present invention is capable of screening at least one of a cancer cell proliferation inhibitor and an anti-cancer agent that specifically inhibit proliferation of a cancer cell without inhibiting proliferation of a normal cell.

<3D Cell Culture Step>

The 3D cell culture step is a step of culturing a NIH3T3 cell expressing an epidermal growth factor receptor mutant vIII (hereinafter may be referred to as "NIH3T3/EGFR vIII cell") in a medium including a test substance under an environment without an adhesion scaffold.

In the 3D cell culture step, a normal cell is not capable of being proliferated, but a cancer cell is capable of being proliferated (hereinafter may be referred to as "having a scaffold-independent proliferation capacity"). Therefore, in the 3D cell culture step, the presence or absence of proliferation inhibiting activity of a test substance against a cancer cell is capable of being examined.

—Environment Without Adhesion Scaffold—

The environment without an adhesion scaffold is not particularly limited and may be appropriately selected depending on the intended purpose. For example, incubators of which cell-contacting surfaces are subjected to ultra-low attachment surface treatment, or soft agar media may be used.

Specific examples of the incubators of which cell-contacting surfaces are subjected to ultra-low attachment surface treatment include 96 Well Ultra Low Attachment Microplate (Product #3474, available from Corning Inc.) and 100 mm Ultra Low Attachment Culture Dish (Product #3262, available from Corning Inc.).

—Other Culture Conditions—

Other culture conditions are not particularly limited and may be appropriately selected from known culture conditions. For example, culture may be performed at 37° C. in the presence of 5% carbon dioxide.

A culture period of the 3D cell culture step is not particularly limited and may be appropriately selected depending on the intended purpose, but is preferably 1 to 10 days, more preferably 2 to 4 days.

—Test Substance—

The test substance is not particularly limited and may be appropriately selected depending on the intended purpose. Examples thereof include compounds, derivatives of the compounds, plant extracts, and proteins.

An amount of the test substance to be added to a medium is not particularly limited and may be appropriately selected depending on the intended purpose. Examples thereof include 0.00001 µM to 100 µM.

—Medium—

The medium is not particularly limited and may be appropriately selected depending on the intended purpose. Examples thereof include Dulbecco's Modified Eagle Medium supplemented with 5% FBS.

—NIH3T3/EGFR vIII Cell—

The NIH3T3/EGFR vIII cell is a cell expressing an epidermal growth factor receptor mutant vIII in which exons 2 to 7 are deleted. For example, it may be prepared according to "Jpn. J. Cancer Res, 81, 773-779, 1990."

The number of cells to be seeded is not particularly limited and may be appropriately selected depending on the intended purpose. For example, when a 96-well plate is used, 5,000 to 25,000 cells per well may be seeded.

A sequence of the 3D cell culture step and a 2D cell culture step described below is not particularly limited and may be appropriately selected depending on the intended purpose. For example, the 3D cell culture step may be performed in advance of the 2D cell culture step, the 2D cell culture step may be performed in advance of the 3D cell culture step, or both steps may be performed simultaneously.

<2D Cell Culture Step>

The 2D cell culture step is a step of culturing a NIH3T3 cell in a medium including a test substance under an environment with an adhesion scaffold.

In the 2D cell culture step, a normal cell is capable of being proliferated. Therefore, in the 2D cell culture step, the presence or absence of proliferation inhibiting activity of a test substance against a normal cell is capable of being examined.

—Environment with Adhesion Scaffold—

The environment with an adhesion scaffold is not particularly limited and may be appropriately selected depending on the intended purpose. For example, incubators of which cell-contacting surfaces are subjected to attachment surface treatment, or soft agar media may be used.

Specific examples of the incubators of which cell-contacting surfaces are subjected to attachment surface treatment include 96 Well Clear Flat Bottom TC-Treated Microplate (Product #3585, available from Corning Inc.).

—Other Culture Conditions—

Other culture conditions are not particularly limited and may be appropriately selected from known culture conditions. For example, the other culture conditions may be the same as those described under the section entitled "Other culture conditions" for the 3D cell culture step.

—Test Substance—

A test substance and an amount of the test substance to be added to a medium are not particularly limited and may be appropriately selected depending on the intended purpose. For example, they may be the same as those described under the section entitled "Test substance" for the 3D cell culture step.

—Medium—

The medium is not particularly limited and may be appropriately selected depending on the intended purpose. For example, they may be the same as those described under the section entitled "Medium" for the 3D cell culture step.

—NIH3T3 Cell—

The NIH3T3 cell is a cultured cell isolated from mouse fetal skin and a cell having both of normal cell properties and a cancer cell-like immortalization property.

The NIH3T3 cell may be available from, for example, ATCC (American Type Culture Collection).

The number of cells to be seeded is not particularly limited and may be appropriately selected depending on the intended purpose. For example, when a 96 well plate is used, 1,000 to 3,000 cells are seeded per well.

<Evaluation Step>

The evaluation step is a step of evaluating a test substance as having an activity as at least one of the cancer cell proliferation inhibitor and the anti-cancer agent when the test substance does not inhibit proliferation of the NIH3T3 cell in the 2D cell culture step, but inhibits proliferation of the NIH3T3 cell expressing an epidermal growth factor receptor mutant vIII in the 3D cell culture step.

A method for determining whether proliferation of cells is inhibited in each of the cell culture steps is not particularly limited and may be appropriately selected depending on the intended purpose.

For example, the number of viable cells after each of the cell culture steps is counted and a cell proliferation inhibition rate and thus $IC_{50}$ are calculated. Whether proliferation of cells is inhibited may be determined based on the value of $IC_{50}$. Specifically, when the $IC_{50}$ is less than 10 it may be determined that the proliferation of cells is inhibited by the test substance. When the $IC_{50}$ is more than 10 µM, it may be determined that the proliferation of cells is not inhibited by the test substance.

A method for counting the number of viable cells is not particularly limited and may be appropriately selected from known methods. Examples thereof include CELLTITER-GLO (trademark) Luminescent Cell Viability Assay (available from Promega), which is a method for quantitating ATP in viable cells, and CELLTITER 96 (registered trademark) Aqueous One Solution Cell Proliferation Assay (available from Promega).

In the evaluation step, a test substance having $IC_{50}$ of less than 1 µM in the 3D cell culture step and $IC_{50}$ of more than 10 µM in the 2D cell culture step is preferably evaluated as having an activity as at least one of the cancer cell proliferation inhibitor and the anti-cancer agent; a test substance having $IC_{50}$ of less than 0.5 µM in the 3D cell culture step and $IC_{50}$ of more than 10 µM in the 2D cell culture step is more preferably evaluated as having an activity as at least one of the cancer cell proliferation inhibitor and the anti-cancer agent; a test substance having $IC_{50}$ of less than 0.1 µM in the 3D cell culture step and $IC_{50}$ of more than 10 µM in the 2D cell culture step is further preferably evaluated as having an activity as at least one of the cancer cell proliferation inhibitor and the anti-cancer agent; and a test substance having $IC_{50}$ of less than 0.05 µM in the 3D cell culture step and $IC_{50}$ of more than 10 µM in the 2D cell culture step is particularly preferably evaluated as having an activity as at least one of the cancer cell proliferation inhibitor and the anti-cancer agent.

<Other Steps>

The other steps are not particularly limited and may be appropriately selected depending on the intended purpose, so long as they do not impair effects of the present invention. Examples thereof include a step of preparing a NIH3T3 cell expressing an epidermal growth factor receptor mutant vIII used in the 3D cell culture step and a step of preparing a NIH3T3 cell used in the 2D cell culture step.

A method for preparing each of the cells is not particularly limited and may be appropriately selected from known culture methods.

According to the screening method of the present invention, as demonstrated in Test Examples described below, a test substance having proliferation inhibiting activity against not only a cancer cell expressing an epidermal growth factor receptor mutant vIII, but also a cancer cell overexpressing a wild-type epidermal growth factor receptor is capable of being screened.

When the cancer cell overexpressing a wild-type epidermal growth factor receptor is used for screening, an epidermal growth factor, which is a ligand of the epidermal growth factor receptor, is needed to be added to a medium. According to the screening method of the present invention, however, the ligand is not needed to be added. Therefore, a test substance having an activity as at least one of the cancer cell proliferation inhibitor and the anti-cancer agent is capable of being efficiently screened.

EXAMPLES

The present invention will now be specifically described with reference to Test Examples, but the present invention is not limited thereto in any way.

Test Example 1: Examination of Screening System

Proliferation of each of the below-described cells under an environment without an adhesion scaffold was examined.
<Cell>
(1) NIH3T3 cells expressing epidermal growth factor receptor mutant vIII gene
   The NIH3T3/EGFR vIII cells were prepared according to "Jpn. J. Cancer Res, 81, 773-779, 1990."
(2) Cells overexpressing wild-type epidermal growth factor receptor (hereinafter may be referred to as "NIH3T3/EGFRWT cell")
   The NIH3T3/EGFRWT cells were prepared according to "Jpn. J. Cancer Res, 81, 773-779, 1990."
(3) Mouse NIH3T3 cells (obtained from ATCC, hereinafter may be referred to as "NIH3T3 cell")
<Culture>
Each of the cells was cultured in the following manner.
The cells were seeded to 96 Well Ultra Low Attachment Microplate (Product #3474, available from Corning Inc.) at 10,000 cells/well and cultured at 37° C. in the presence of 5% $CO_2$ in Dulbecco's Modified Eagle Medium supplemented with 5% FBS.

Note that, the NIH3T3/EGFRWT cells were cultured in a medium including 50 ng/mL of an epidermal growth factor and in a medium without epidermal growth factor.

The number of viable cells was counted by CELLTITER-GLO (trademark) Luminescent Cell Viability Assay (available from Promega), which was a method for quantitating ATP in viable cells, 3 days, 4 days, 5 days, 6 days, and 7 days after initiation of culture. The results are presented in FIG. 1.

In FIG. 1, "○ (white circle)" represents the results of culture of the NIH3T3/EGFR vIII cells, "● (black circle)" represents the results of culture of the NIH3T3/EGFRWT cells cultured in an EGF-including medium, "△ (white up-pointing triangle)" represents the results of culture of the NIH3T3/EGFRWT cells cultured in an EGF-free medium, and "□ (white square)" represents the results of culture of the NIH3T3 cells.

In FIG. 1, the number of cells at each measurement time is expressed in percentage, assuming that the number of cells at a time when the cells were seeded to the 96 well plate is 100%.

It was confirmed from the results of FIG. 1 that the NIH3T3/EGFRWT cells cultured in the EGF-free medium and the NIH3T3 cells were decreased in number, but the NIH3T3/EGFRWT cells cultured in the EGF-including medium and the NIH3T3/EGFR vIII cells were grown and proliferated.

Test Example 2: Screening

Each of the below-described compounds as a test substance was screened. Note that, AG1478, Gefitinib, and Erlotinib are known as EGFR kinase inhibitors.
<Compound>
Compound represented by Structural Formula (1)
(3-(2-amino-5-bromophenyl)-2(1H)-quinoxalinone, available from IWAI CHEMICALS COMPANY LTD. or synthesized according to "Synthetic Communications 2011, 41, 1650.").

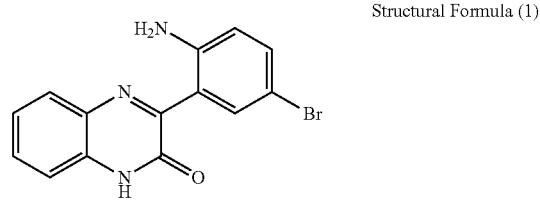 [SMILES: Nc1ccc(Br)cc1-c1nc2ccccc2[nH]c1=O]

Structural Formula (1)

Compound represented by Structural Formula (2)
(3-(2-amino-5-bromophenyl)-7-methylhydroquinoxalin-2-one, available from Enamine)

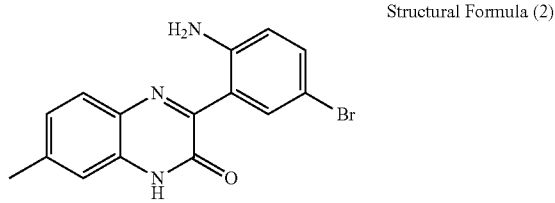 [SMILES: Cc1ccc2nc(-c3cc(Br)ccc3N)c(=O)[nH]c2c1]

Structural Formula (2)

Compound represented by Structural Formula (3)
(N-[4-bromo-2-(3-oxo(4-hydroquinoxalin-2-yl))phenyl]acetamide, available from Life Chemicals)

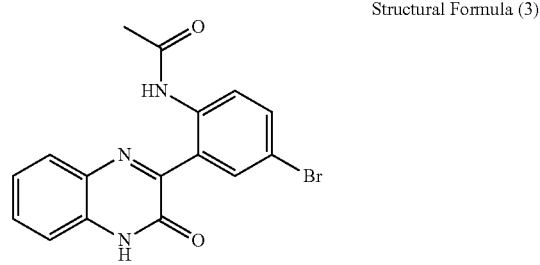 [SMILES: CC(=O)Nc1ccc(Br)cc1-c1nc2ccccc2[nH]c1=O]

Structural Formula (3)

Compound represented by Structural Formula (4)
(3-(2-amino-5-methylphenyl)hydroquinoxalin-2-one, available from Pharmeks)

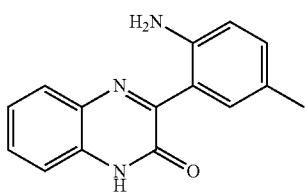

Structural Formula (4)

Compound represented by Structural Formula (5)
(4-{N-[4-bromo-2-(3-oxo(4-hydroquinoxalin-2-yl))phenyl]carbamoyl}butanoic acid, available from Life Chemicals)

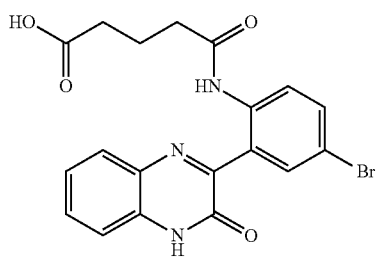

Structural Formula (5)

Compound represented by Structural Formula (6)
(3-(2-amino-5-chlorophenyl)hydroquinoxalin-2-one, available from U.O.S.)

Structural Formula (6)

Compound represented by Structural Formula (7)
(3-(2-Amino-5-fluorophenyl)-2(1H)-quinoxalinone, synthesized according to "Synthetic Communications 2011, 41, 1650.")

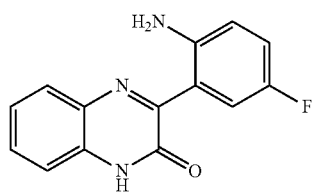

Structural Formula (7)

Compound represented by Structural Formula (8)
(3-(2-Amino-5-iodophenyl)-2(1H)-quinoxalinone)

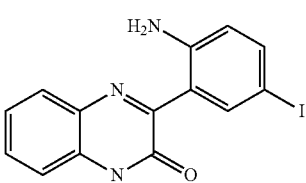

Structural Formula (8)

The compound represented by Structural Formula (8) was synthesized in the following manner with reference to "Synthetic Communications 2011, 41, 1650."

Acetic acid (1.5 mL) was added to 5-iodoisatin (81.9 mg, 0.30 mmol) (available from Aldrich) and 1,2-phenylenediamine (32.4 mg, 0.30 mmol) (available from Tokyo Chemical Industry Co., Ltd.), followed by stirring at room temperature for 2 days. After reaction, the resultant reaction product was azeotroped with toluene. The resultant orange solid was purified by preparative thin-layer chromatography [hexane:ethyl acetate=1:1 (volume ratio)]. Thus, the compound represented by Structural Formula (8) was obtained as an orange solid (18.4 mg, yield: 16.9%).

The thus-obtained compound was measured by 1H NMR, $^{13}$C-NMR, COSY, HMQC, HMBC, and HRMS. The results are described below. Based on these results, the compound was confirmed to have the structure represented by Structural Formula (8).

$^{1}$H NMR (600 MHz, DMSO-$d_6$): δ 6.64 (2H, br. s, NH$_2$), 6.65, (1H, d, J=4.0 Hz, H-3'), 7.28 (1H, dt, J=4.0, 4.0 and 0.5 Hz, H-6), 7.30 (1H, dd, J=4.0 and 0.5 Hz, H-8), 7.38 (1H, dd, J=4.0 and 1.0 Hz, H-4'), 7.49 (1H, dt, J=4.0, 4.0 and 0.5 Hz, H-7), 7.79 (1H, dd, J=4.0 and 0.5 Hz, H-5), 8.41 (1H, d, J=1.5 Hz, H-6') and 12.50 (1H, bs, NH).

$^{13}$C NMR (150.9 MHz, DMSO-$d_6$): δ 74.75 (C-5'), 115.41 (C-8), 118.68 (C-3'), 120.04 (C-1'), 123.03 (C-6), 128.09 (C-5), 129.79 (C-7), 131.30 (C-4a and -8a), 138.37 (C-4'), 138.99 (C-6'), 148.40 (C-2'), 154.16 (C-3) and 155.06 (C-2).

HRMS m/z Found 363.9944 (M+H)+, Calcd. 363.9941.

Compound represented by Structural Formula (9)
(3-(2-aminophenyl)-2(1H)-quinoxalinone, available from Chem Bridge Screening Libraries)

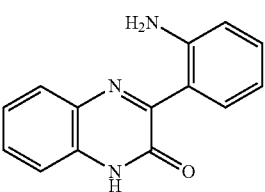

Structural Formula (9)

Compound represented by Structural Formula (10) (3-[5-bromo-2-(methylamino)phenyl]-2(1H)-quinoxalinone, available from Chem Bridge Screening Libraries)

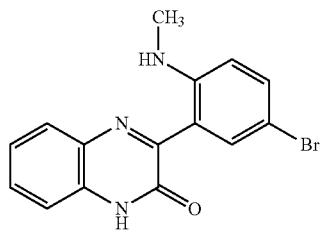

Structural Formula (10)

Compound represented by Structural Formula (11) (3-[2-(ethylamino)phenyl]-2(1H)-quinoxalinone, available from Chem Bridge Screening Libraries)

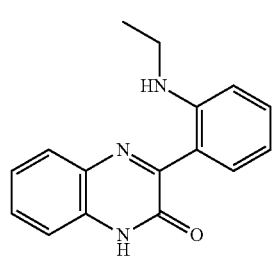

Structural Formula (11)

Compound represented by Structural Formula (12) (3-{2-[(4-fluorobenzyl)amino]phenyl}-2(1H)-quinoxalinone, available from Chem Bridge Screening Libraries)

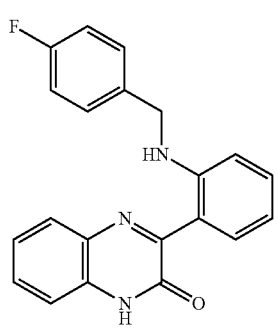

Structural Formula (12)

Compound represented by Structural Formula (13) (3-(2-aminophenyl)-1-methyl-2(1H)-quinoxalinone, available from Chem Bridge Screening Libraries)

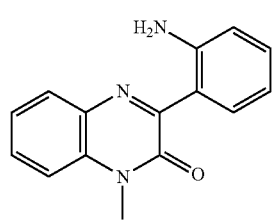

Structural Formula (13)

Compound represented by Structural Formula (14) (ethyl 2-[3-(2-amino-5-bromophenyl)-2-oxohydroquinoxalinyl] acetate, available from Pharmeks)

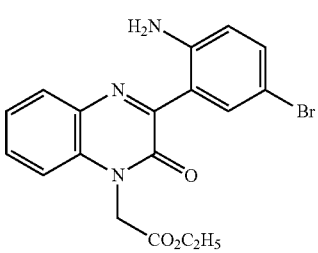

Structural Formula (14)

Compound represented by Structural Formula (15) (N-[4-bromo-2-(3-oxo(4-hydroquinoxalin-2-yl)phenyl]benzamide, available from Life Chemicals)

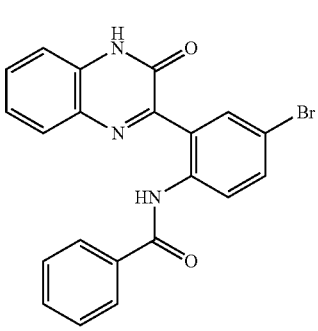

Structural Formula (15)

AG1478 (available from WAKO)

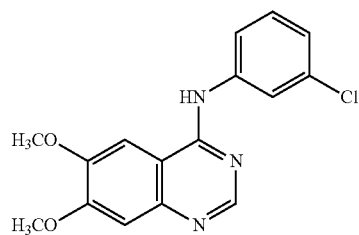 [SMILES: COc1cc2ncnc(Nc3cccc(Cl)c3)c2cc1OC]

Gefitinib (available from AstraZeneca K.K.)

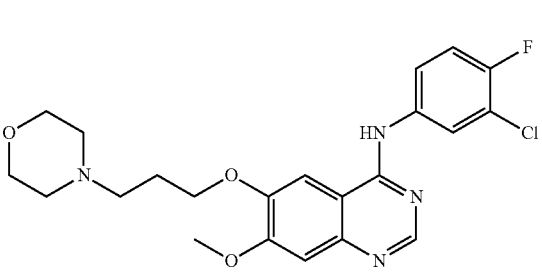 [SMILES: COc1cc2ncnc(Nc3ccc(F)c(Cl)c3)c2cc1OCCCN1CCOCC1]

Erlotinib (available from Chemie Tek)

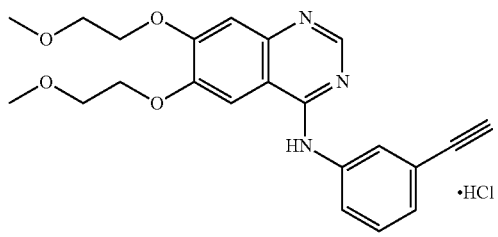 [SMILES: C#Cc1cccc(Nc2ncnc3cc(OCCOC)c(OCCOC)cc23)c1 ; Cl]

<3D Cell Culture Step>

The NIH3T3/EGFR vIII cells at 2×10⁴ cells/100 μL were seeded to 96 Well Ultra Low Attachment Microplate (Product #3474, available from Corning Inc.) in a volume of 100 μL per well, added with a test substance at a predetermined concentration, and cultured at 37° C. in the presence of 5% $CO_2$ for 3 days.

Note that, as a negative control, the NIH3T3 cells at 2×10⁴ cells/100 were seeded to the same plate in a volume of 1004 per well and cultured at 37° C. in the presence of 5% $CO_2$ for 3 days without the addition of the test substance.

Note that, Dulbecco's Modified Eagle Medium supplemented with 5% FBS was used for the culture.

—Measurement of Cell Proliferation Inhibition Rate—

After the 3 days of culture, the number of viable cells was counted by CELLTITER-GLO (trademark) Luminescent Cell Viability Assay (available from Promega), which was a method for quantitating ATP in viable cells. A cell proliferation inhibition rate in the 3D cell culture step was calculated according to (Expression 1) below. The values of $IC_{50}$ are presented in Table 1.

Cell proliferation inhibition rate(%)=[1−{(A−B)/(C−B)}]×100     (Expression 1)

In the (Expression 1), A denotes the number of viable NIH3T3/EGFR vIII cells when the test substance was added, B denotes the number of viable NIH3T3 cells when the test substance was not added, and C denotes the number of viable NIH3T3/EGFR vIII cells when the test substance was not added.

<2D Cell Culture Step>

The NIH3T3 cells at 2×10³ cells/100 μL were seeded to 96 Well Clear Flat Bottom TC-Treated Microplate (Product #3585, available from Corning Inc.) in a volume of 1004 per well, added with a test substance at a predetermined concentration, and cultured at 37° C. in the presence of 5% $CO_2$ for 3 days.

Note that, as a negative control, the NIH3T3 cells at 2×10³ cells/100 were seeded to the same plate in a volume of 100 μL per well and cultured at 37° C. in the presence of 5% $CO_2$ for 3 days without the addition of the test substance.

Note that, Dulbecco's Modified Eagle Medium supplemented with 5% FBS was used for the culture.

—Measurement of Cell Proliferation Inhibition Rate—

After the 3 days of culture, the number of viable cells was counted by CELLTITER-GLO (trademark) Luminescent Cell Viability Assay (available from Promega), which was a method for quantitating ATP in viable cells. A cell proliferation inhibition rate in the 2D cell culture step was calculated according to (Expression 2) below. The values of $IC_{50}$ are presented in Table 1.

Cell proliferation inhibition rate(%)=(1−D/E)×100     (Expression 2)

In the (Expression 2), D denotes the number of viable NIH3T3 cells when the test substance was added, and E denotes the number of viable NIH3T3 cells when the test substance was not added.

TABLE 1

| Compound | $IC_{50}$ (μM) | |
|---|---|---|
| | 3D cell culture step | 2D cell culture step |
| Structural Formula (1) | 0.012 | >10 |
| Structural Formula (2) | 0.1 | >10 |
| Structural Formula (3) | 0.5 | >10 |
| Structural Formula (4) | 0.5 | >10 |
| Structural Formula (5) | 0.4 | >10 |
| Structural Formula (6) | 0.014 | >10 |
| Structural Formula (7) | 0.34 | >10 |
| Structural Formula (8) | 0.01 | >10 |
| Structural Formula (9) | >10 | >10 |
| Structural Formula (10) | >10 | >10 |
| Structural Formula (11) | >10 | >10 |
| Structural Formula (12) | >10 | >10 |
| Structural Formula (13) | >10 | >10 |
| Structural Formula (14) | 10 | >10 |
| Structural Formula (15) | >10 | >10 |
| AG1478 | 1 | 50 |
| Gefitinib | 1 | >50 |
| Erlotinib | 1 | 50 |

<Evaluation Step>

It was confirmed from the results of Table 1 that AG1478, Gefitinib, and Erlotinib, which were known as EGFR kinase inhibitors, inhibited proliferation of the NIH3T3 cells expressing an epidermal growth factor receptor mutant vIII in the 3D cell culture step at the concentration at which proliferation of the cells were not inhibited in the 2D cell culture step. This indicates that the present screening system is effective.

It was also found that the compounds represented by Structural Formulae (1) to (8) did not inhibit proliferation of the NIH3T3 cells, but was capable of inhibiting proliferation of the NIH3T3 cells expressing an epidermal growth factor receptor mutant vIII. Among the compounds represented by Structural Formulae (1) to (8), the compounds represented by Structural Formulae (1), (6), and (8) were particularly excellent and exhibited a more significant cell proliferation inhibiting activity than those of the AG1478, Gefitinib, and Erlotinib.

It was suggested that the halogen atom at position 5 of the phenyl ring in the compound represented by the Structural Formula (1) was critical for expressing the activity and that alkylation of the amino group at position 2 was not preferable.

Note that, the compound represented by the Structural Formula (1) also inhibited proliferation of the NIH3T3/EGFRWT cells when the 3D cell culture step was performed in the same manner, except that the NIH3T3 cells expressing an epidermal growth factor receptor mutant vIII was changed to the NIH3T3/EGFRWT cells and EGF (50 ng/mL) was added to the medium.

Test Example 3: Inhibition of Proliferation of EGFR vIII Gene Non-Expressing Cells Whether the compound represented by the Structural Formula (1) and AG1478 inhibited proliferation of EGFR vIII gene non-expressing cells under an environment without an adhesion scaffold was examined.

The following 3 brain tumor cells were used as the EGFR vIII gene non-expressing cells.

U251 cells (available from ATCC)
U87MG cells (available from ATCC)
KS-1 cells (available from ATCC)
<3D Cell Culture Step>

The 3D cell culture step was performed in the same manner as in the Test Example 2, except that the brain tumor cells and, as the test substance, the compound represented by the Structural Formula (1) or AG1478 were used.

Note that, the NIH3T3/EGFRWT cells (cultured in an EGF-including medium) and the NIH3T3/EGFR vIII cells were also tested in the same manner.

—Measurement of Cell Proliferation Inhibition Rate—

After the 3 days of culture, the number of viable cells was counted by CELLTITER-GLO (trademark) Luminescent Cell Viability Assay (available from Promega), which was a method for quantitating ATP in viable cells. A cell proliferation inhibition rate in the 3D cell culture step was calculated according to (Expression 3) below. The results are presented in FIGS. 2 and 3.

Cell proliferation inhibition rate(%)=(1−$X/Y$)×100   (Expression 3)

In the (Expression 3), X denotes the number of viable cells when the test substance was added, and Y denotes the number of viable cells when the test substance was not added.

Figure 2:
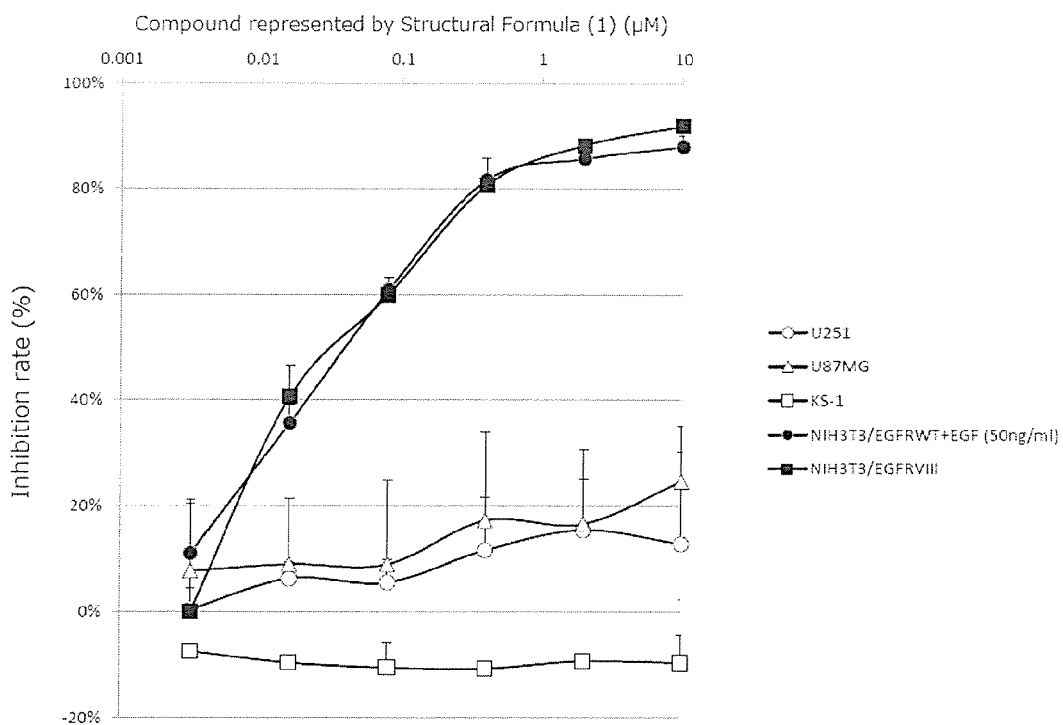
FIG. 2 is a graph illustrating cell proliferation inhibition rates when a compound represented by Structural Formula (1) is used as a test substance in Test Example 3.
Figure 3:
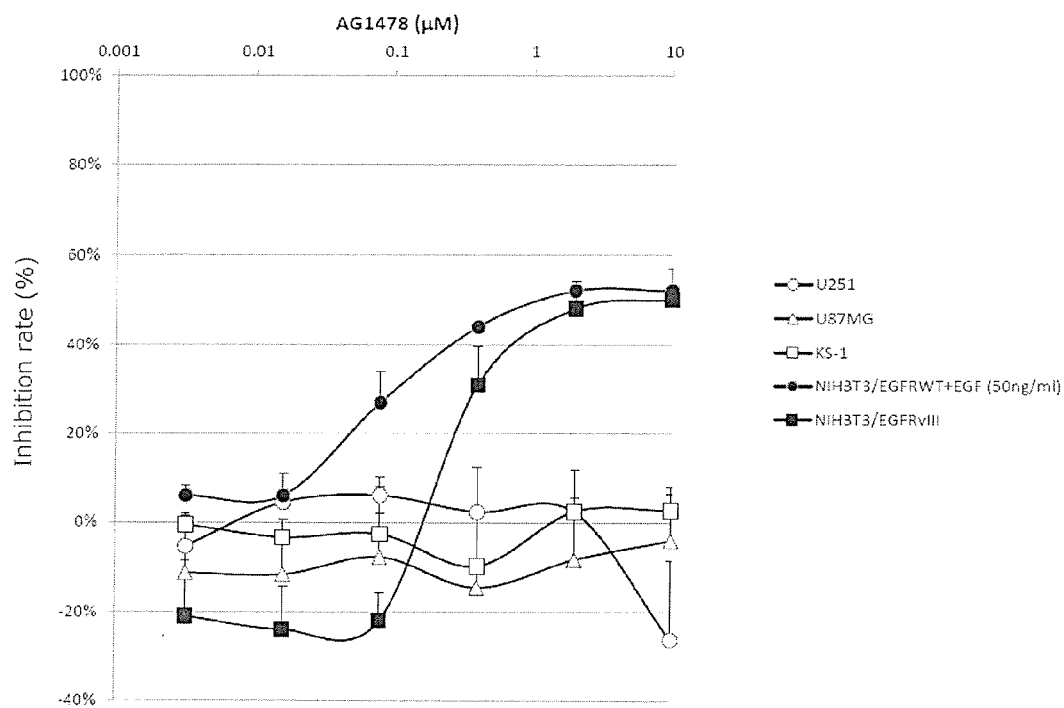
FIG. 3 is a graph illustrating cell proliferation inhibition rates when AG1478 is used as a test substance in Test Example 3.

FIG. 2 is a graph illustrating cell proliferation inhibition rates when the compound represented by Structural Formula (1) is used as the test substance. FIG. 3 is a graph illustrating cell proliferation inhibition rates when AG1478 is used as the test substance.

In FIGS. 2 and 3, "○ (white circle), solid line" represents the results of the U251 cells, "△ (white up-pointing triangle), solid line" represents the results of the U87MG cells, "□ (white square), solid line" represents the results of the KS-1 cells, "●(black circle), solid line" represents the results of the NIH3T3/EGFRWT cells, and "■(black square), solid line" represents the results of the NIH3T3/EGFR vIII cells.

For the results of FIGS. 2 and 3, the compound represented by the Structural Formula (1) exhibited an inhibiting activity against a scaffold-independent proliferation capacity in the NIH3T3/EGFRWT cells and the NIH3T3/EGFR vIII cells, but did not exhibit an inhibiting activity against a scaffold-independent proliferation capacity in the U251 cells, the U87MG cells, and the KS-1 cells. This was also applied to AG1478. Therefore, the possibility was suggested that, likewise AG1478, the compound represented by the Structural Formula (1) inhibited scaffold-independent proliferation depending on EGFR vIII or wild-type EGFR.

Test Example 4: Acute Toxicity Test

Test Example 4-1: Intraperitoneal Administration

The compounds represented by the Structural Formula (1) at various concentrations, which were produced by dissolving in physiological saline including 10% by mass of DMSO and 1% by mass of TWEEN80, were intraperitoneally administered once to 4 week-old female ICR mice. Thereafter, the mice were observed for changes in body weight for 2 weeks. The results are presented in FIG. 4-1.

Figures 1, 4:
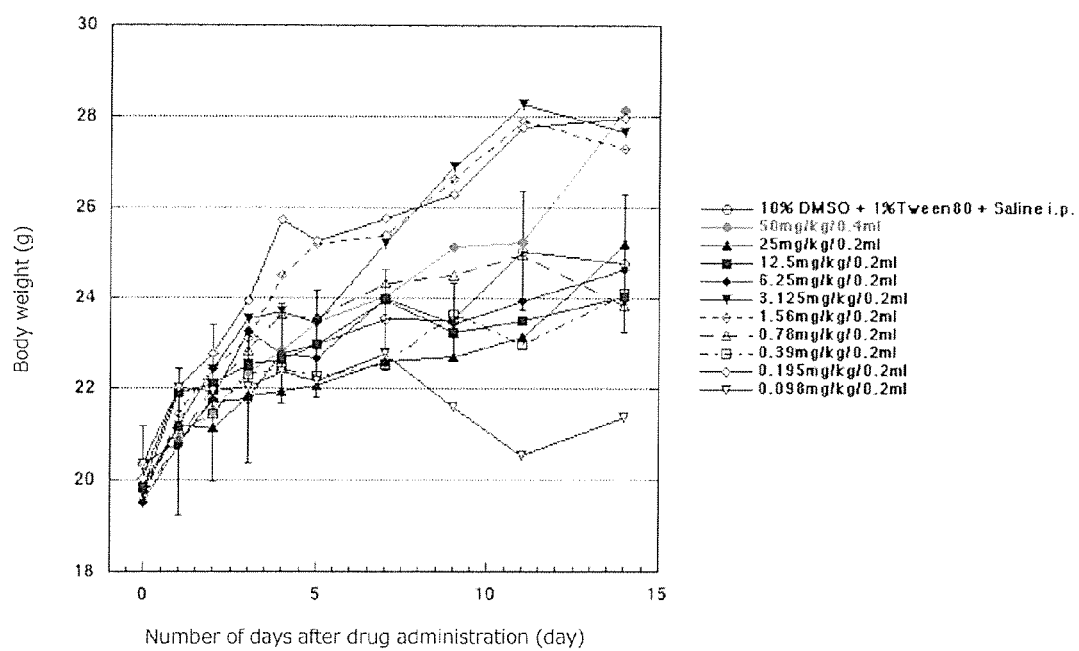
Figures 2, 4:
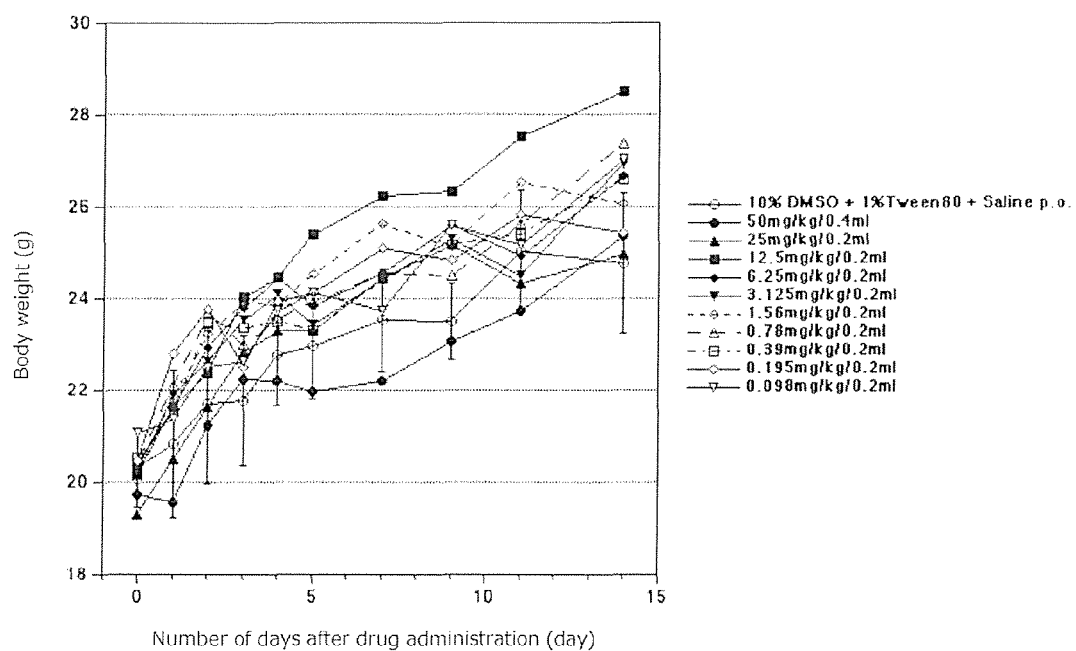
Figures 3, 4:
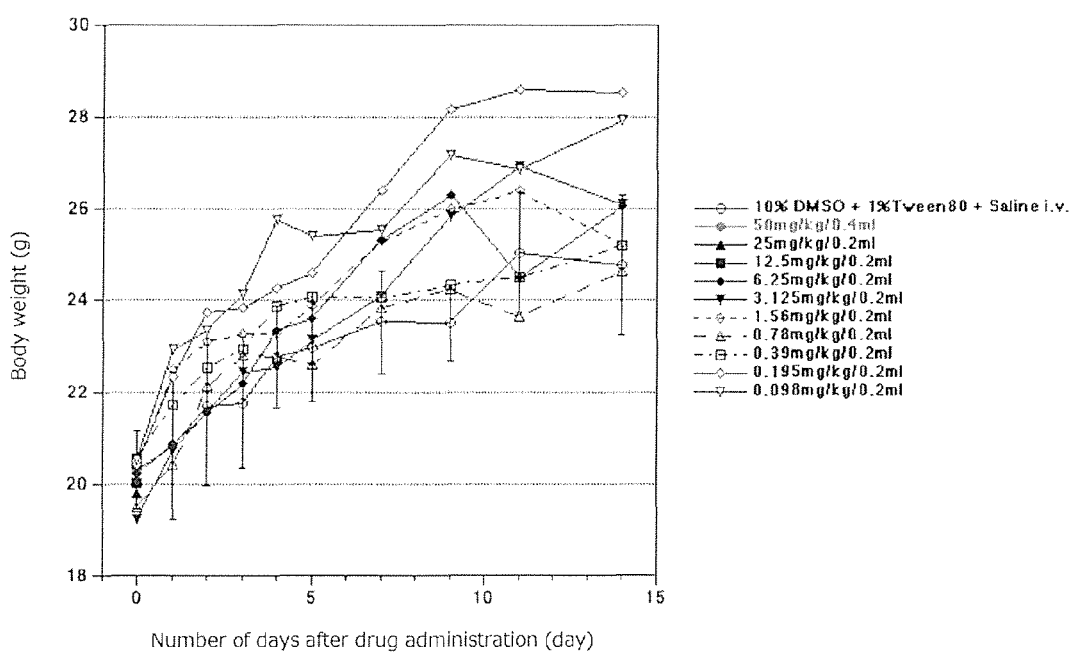

In FIG. 4-1, "● (black circle), solid line" represents the results when the compound represented by the Structural Formula (1) was administered at 50 mg/kg/0.4 mL, "▲ (black up-pointing triangle), solid line" represents the results when the compound represented by the Structural Formula (1) was administered at 25 mg/kg/0.2 mL, "■ (black square), solid line" represents the results when the compound represented by the Structural Formula (1) was administered at 12.5 mg/kg/0.2 mL, "♦ (black diamond), solid line" represents the results when the compound represented by the Structural Formula (1) was administered at 6.25 mg/kg/0.2 mL, "▼ (black down-pointing triangle), solid line" represents the results when the compound represented by the Structural Formula (1) was administered at 3.125 mg/kg/0.2 mL, "◇ (white diamond), dashed line" represents the results when the compound represented by the Structural Formula (1) was administered at 1.56 mg/kg/0.2 mL, "△ (white up-pointing triangle), dashed line" represents the results when the compound represented by the Structural Formula (1) was administered at 0.78 mg/kg/0.2 mL, "□ (white square), dashed line" represents the results when the compound represented by the Structural Formula (1) was administered at 0.39 rag/kg/0.2 mL, "◇ (white diamond), solid line" represents the results when the compound represented by the Structural Formula (1) was administered at 0.195 mg/kg/0.2 mL, and "▽ (white down-pointing triangle), solid line" represents the results when the compound represented by the Structural Formula (1) was administered at 0.098 mg/kg/0.2 mL. Note that, "○ (white circle), solid line" represents the results when the physiological saline including 10% by mass of DMSO and 1% by mass of TWEEN80 was intraperitoneally administered.

Two-weeks after the compounds represented by the Structural Formula (1) at the above concentrations were intraperitoneally administered, the mice were dissected and organs thereof were weighed. The results are presented in Table 2-1.

TABLE 2-1

| | | Organ weight (mg) | | | | | | |
|---|---|---|---|---|---|---|---|---|
| | | Thymus | Heart | Lung | Liver | Spleen | Kidney (Right) | Kidney (Left) |
| A | Mean | 77.0 | 111.7 | 157.3 | 1380.0 | 127.7 | 165.0 | 163.0 |
| | S.D. | 15.1 | 5.9 | 2.1 | 126.8 | 29.7 | 17.1 | 17.5 |
| 50 mg/kg/0.4 mL | | 69.0 | 120.0 | 168.0 | 1747.0 | 132.0 | 173.0 | 166.0 |
| 25 mg/kg/0.2 mL | | 92.0 | 111.0 | 147.0 | 1316.0 | 98.0 | 170.0 | 157.0 |
| 12.5 mg/kg/0.2 mL | | 63.0 | 107.0 | 159.0 | 1120.0 | 98.0 | 163.0 | 161.0 |
| 6.25 mg/kg/0.2 mL | | 68.0 | 114.0 | 178.0 | 1412.0 | 104.0 | 163.0 | 167.0 |
| 3.125 mg/kg/0.2 mL | | 99.0 | 135.0 | 179.0 | 1558.0 | 150.0 | 191.0 | 193.0 |
| 1.56 mg/kg/0.2 mL | | 85.0 | 134.0 | 178.0 | 1472.0 | 103.0 | 169.0 | 162.0 |
| 0.78 mg/kg/0.2 mL | | 78.0 | 115.0 | 167.0 | 1263.0 | 116.0 | 159.0 | 163.0 |
| 0.39 mg/kg/0.2 mL | | 74.0 | 106.0 | 160.0 | 1350.0 | 95.0 | 168.0 | 157.0 |
| 0.195 mg/kg/0.2 mL | | 83.0 | 125.0 | 169.0 | 1590.0 | 121.0 | 184.0 | 175.0 |
| 0.098 mg/kg/0.2 mL | | 67.0 | 115.0 | 160.0 | 1047.0 | 78.0 | 147.0 | 139.0 |

In Table 2-1, A represents the results when the physiological saline including 10% by mass of DMSO and 1% by mass of TWEEN80 was administered.

Test Example 4-2: Oral Administration

The compounds represented by the Structural Formula (1) at various concentrations, which were produced by dissolving in physiological saline including 10% by mass of DMSO and 1% by mass of TWEEN80, were orally administered once to 4 week-old female TCR mice. Thereafter, the mice were observed for changes in body weight for 2 weeks. The results are presented in FIG. 4-2.

In FIG. 4-2, "● (black circle), solid line" represents the results when the compound represented by the Structural Formula (1) was administered at 50 mg/kg/0.4 mL, "▲ (black up-pointing triangle), solid line" represents the results when the compound represented by the Structural Formula (1) was administered at 25 mg/kg/0.2 mL, "■ (black square), solid line" represents the results when the compound represented by the Structural Formula (1) was administered at 12.5 mg/kg/0.2 mL, "♦ (black diamond), solid line" represents the results when the compound represented by the Structural Formula (1) was administered at 6.25 mg/kg/0.2 mL, "▼ (black down-pointing triangle), solid line" represents the results when the compound represented by the Structural Formula (1) was administered at 3.125 mg/kg/0.2 mL, "◇ (white diamond), dashed line" represents the results when the compound represented by the Structural Formula (1) was administered at 1.56 rag/kg/0.2 mL, "△ (up-pointing triangle), dashed line" represents the results when the compound represented by the Structural Formula (1) was administered at 0.78 mg/kg/0.2 mL, "□ (white square), dashed line" represents the results when the compound represented by the Structural Formula (1) was administered at 0.39 mg/kg/0.2 mL, "◇ (white diamond), solid line" represents the results when the compound represented by the Structural Formula (1) was administered at 0.195 mg/kg/0.2 mL, and "▽ (white down-pointing triangle), solid line" represents the results when the compound represented by the Structural Formula (1) was administered at 0.098 mg/kg/0.2 mL. Note that, "○ (white circle), solid line" represents the results when the physiological saline including 10% by mass of DMSO and 1% by mass of TWEEN80 was orally administered.

Two-weeks after the compounds represented by the Structural Formula (1) at the above concentrations were orally administered, the mice were dissected and organs thereof were weighed. The results are presented in Table 2-2.

In Table 2-2, A represents the results when the physiological saline including 10% by mass of DMSO and 1% by mass of TWEEN80 was administered.

Test Example 4-3: Tail Vein Administration

The compounds represented by the Structural Formula (1) at various concentrations, which were produced by dissolving in physiological saline including 10% by mass of DMSO and 1% by mass of TWEEN80, were administered once to the tail veins of 4 week-old female ICR mice. Thereafter, the mice were observed for changes in body weight for 2 weeks. The results are presented in FIG. 4-3.

In FIG. 4-3, "● (black circle), solid line" represents the results when the compound represented by the Structural Formula (1) was administered at 50 mg/kg/0.4 mL, "▲ (black triangle), solid line" represents the results when the compound represented by the Structural Formula (1) was administered at 25 mg/kg/0.2 mL, "■ (black square), solid line" represents the results when the compound represented by the Structural Formula (1) was administered at 12.5 mg/kg/0.2 mL, "♦ (black diamond), solid line" represents the results when the compound represented by the Structural Formula (1) was administered at 6.25 mg/kg/0.2 mL, "▼ (black down-pointing triangle), solid line" represents the results when the compound represented by the Structural Formula (1) was administered at 3.125 mg/kg/0.2 mL, "◇ (white diamond), dashed line" represents the results when the compound represented by the Structural Formula (1) was administered at 1.56 mg/kg/0.2 mL, "△ (white up-pointing triangle), dashed line" represents the results when the compound represented by the Structural Formula (1) was administered at 0.78 mg/kg/0.2 mL, "□ (white square), dashed line" represents the results when the compound represented by the Structural Formula (1) was administered at 0.39 mg/kg/0.2 mL, "◇ (white diamond), solid line" represents the results when the compound represented by the Structural Formula (1) was administered at 0.195 mg/kg/0.2 mL, and "▽ (white down-pointing triangle), solid line" represents the results when the compound represented by the Structural Formula (1) was administered at 0.098 mg/kg/0.2 mL. Note that, "○ (white circle), solid line" represents the results when the physiological saline including 10% by mass of DMSO and 1% by mass of TWEEN80 was administered to the tail veils.

Two-weeks after the compounds represented by the Structural Formula (1) at the above concentrations were administered to the tail veins, the mice were dissected and organs thereof were weighed. The results are presented in Table 2-3.

TABLE 2-2

| | | Organ weight (mg) | | | | | | |
|---|---|---|---|---|---|---|---|---|
| | | Thymus | Heart | Lung | Liver | Spleen | Kidney (Right) | Kidney (Left) |
| A | Mean | 77.0 | 111.7 | 157.3 | 1380.0 | 127.7 | 165.0 | 163.0 |
| | S.D. | 15.1 | 5.9 | 2.1 | 126.8 | 29.7 | 17.1 | 17.5 |
| 50 mg/kg/0.4 mL | | 95.0 | 115.0 | 166.0 | 1403.0 | 117.0 | 155.0 | 150.0 |
| 25 mg/kg/0.2 mL | | 87.0 | 116.0 | 176.0 | 1290.0 | 100.0 | 169.0 | 157.0 |
| 12.5 mg/kg/0.2 mL | | 99.0 | 143.0 | 191.0 | 1327.0 | 173.0 | 177.0 | 177.0 |
| 6.25 mg/kg/0.2 mL | | 112.0 | 122.0 | 169.0 | 1362.0 | 111.0 | 165.0 | 154.0 |
| 3.125 mg/kg/0.2 mL | | 75.0 | 117.0 | 166.0 | 1308.0 | 127.0 | 164.0 | 164.0 |
| 1.56 mg/kg/0.2 mL | | 90.0 | 131.0 | 166.0 | 1283.0 | 120.0 | 183.0 | 166.0 |
| 0.78 mg/kg/0.2 mL | | 98.0 | 116.0 | 174.0 | 1577.0 | 152.0 | 179.0 | 177.0 |
| 0.39 mg/kg/0.2 mL | | 72.0 | 117.0 | 153.0 | 1328.0 | 97.0 | 171.0 | 175.0 |
| 0.195 mg/kg/0.2 mL | | 76.0 | 118.0 | 153.0 | 1258.0 | 89.0 | 186.0 | 172.0 |
| 0.098 mg/kg/0.2 mL | | 97.0 | 124.0 | 163.0 | 1524.0 | 132.0 | 191.0 | 183.0 |

TABLE 2-3

| | | Organ weight (mg) | | | | | | |
|---|---|---|---|---|---|---|---|---|
| | | Thymus | Heart | Lung | Liver | Spleen | Kidney (Right) | Kidney (Left) |
| A | Mean | 77.0 | 111.7 | 157.3 | 1380.0 | 127.7 | 165.0 | 163.0 |
| | S.D. | 15.1 | 5.9 | 2.1 | 126.8 | 29.7 | 17.1 | 17.5 |
| 6.25 mg/kg/0.2 mL | | 69.0 | 113.0 | 176.0 | 1448.0 | 131.0 | 177.0 | 173.0 |
| 3.125 mg/kg/0.2 mL | | 86.0 | 115.0 | 164.0 | 1528.0 | 139.0 | 172.0 | 152.0 |
| 1.56 mg/kg/0.2 mL | | 56.0 | 121.0 | 170.0 | 1471.0 | 104.0 | 167.0 | 170.0 |
| 0.78 mg/kg/0.2 mL | | 112.0 | 116.0 | 164.0 | 1423.0 | 115.0 | 174.0 | 165.0 |
| 0.39 mg/kg/0.2 mL | | 83.0 | 121.0 | 173.0 | 1325.0 | 110.0 | 168.0 | 162.0 |
| 0.195 mg/kg/0.2 mL | | 82.0 | 127.0 | 180.0 | 1652.0 | 113.0 | 193.0 | 182.0 |
| 0.098 mg/kg/0.2 mL | | 84.0 | 116.0 | 164.0 | 1570.0 | 117.0 | 179.0 | 178.0 |

In Table 2-3, A represents the results when the physiological saline including 10% by mass of DMSO and 1% by mass of TWEEN80 was administered.

For the results of the Test Examples 4-1 to 4-3, the compound represented by the Structural Formula (1) was found to have no significant toxicity, except that the compound had poor solubility and therefore the mice were immediately dead due to vascular occlusion when the compound was administered to the tail veins at 12.5 mg/kg to 50 mg/kg.

Test Example 5: Anti-Tumor Effect

Test Example 5-1: NIH3T3/EGFR vIII Cell-Transplanted Tumor

The NIH3T3/EGFR vIII cells were prepared to $1 \times 10^5$ cells/100 µL with 62.5% by volume of MATRIGEL (available from Becton, Dickinson and Company) including a DMEM medium. The resultant preparation was transplanted under the skin of 8 week-old Balb/c Nude mice.

The compound represented by the Structural Formula (1) was intraperitoneally administered once a day from 1 day to day 17 after the transplantation. The compound represented by the Structural Formula (1) was dissolved in physiological saline including 10% by mass of DMSO and 1% by mass of TWEEN80 and administered at a single dose of 30 mg/kg.

As a negative control (Vehicle), the physiological saline including 10% by mass of DMSO and 1% by mass of TWEEN80 was intraperitoneally administered once a day from 1 clay to day 17 after the transplantation.

As a positive control, Gefitinib, which was an EGFR kinase inhibitor and an existing cancer therapeutic drug, was orally administered once a day from 1 day to day 17 after the transplantation. The Gefitinib was administered at a single dose of 100 mg/kg.

Note that, the negative control group included 6 animals per group, the compound represented by the Structural Formula (1) administration group included 5 animals per group, and the positive control group included 5 animals per group.
<Evaluation>

The compound represented by the Structural Formula (1) was evaluated for a tumor inhibiting effect by observing proliferation of the tumors after the cell transplantation.
—Tumor Volume—

After the cell transplantation, long diameters and short diameters of the tumors were measured over time by a caliper. A tumor volume of each of the tumors was calculated according to (Expression 4) below. An average and a standard error of the tumor volumes were calculated. The results are presented in FIG. 5-1.

$$\text{Tumor volume} = \text{Long diameter} \times \text{Short diameter}^2 / 2 \quad \text{(Expression 4)}$$

—Tumor Weight—

Seventeen days after the cell transplantation, the tumors were removed from the mice. The tumors were weighed and an average and a standard error thereof were calculated. The results are presented in FIG. 5-2. The photograph of the removed tumors is presented in FIG. 5-3.
—Change in Weight—

The mice were weighed after the cell transplantation and an average and a standard error of thereof were calculated. The results are presented in FIG. 5-4.

Figures 1, 5:
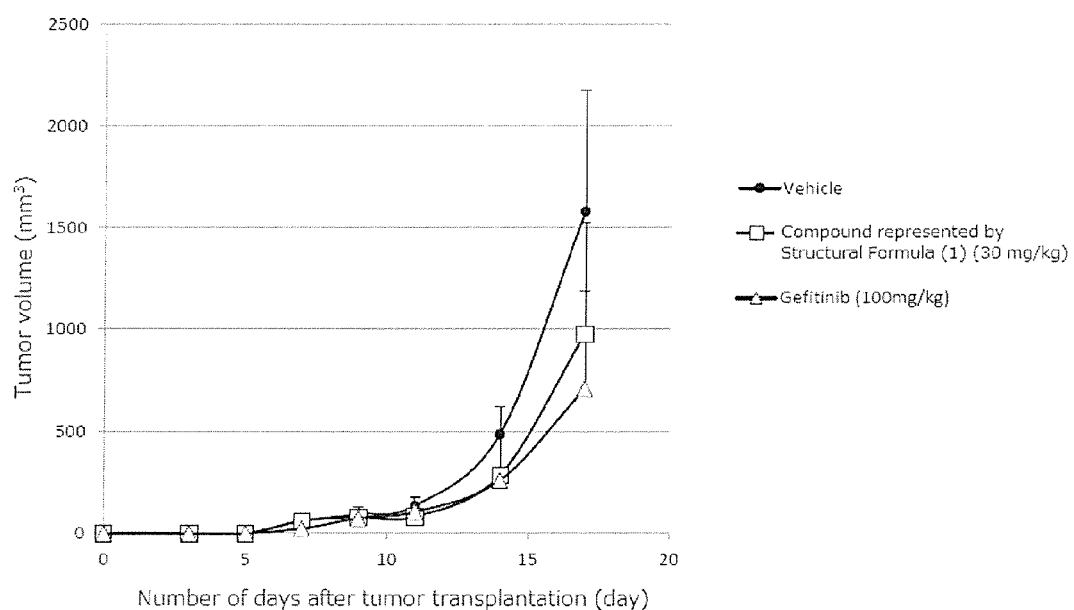
Figures 2, 5:
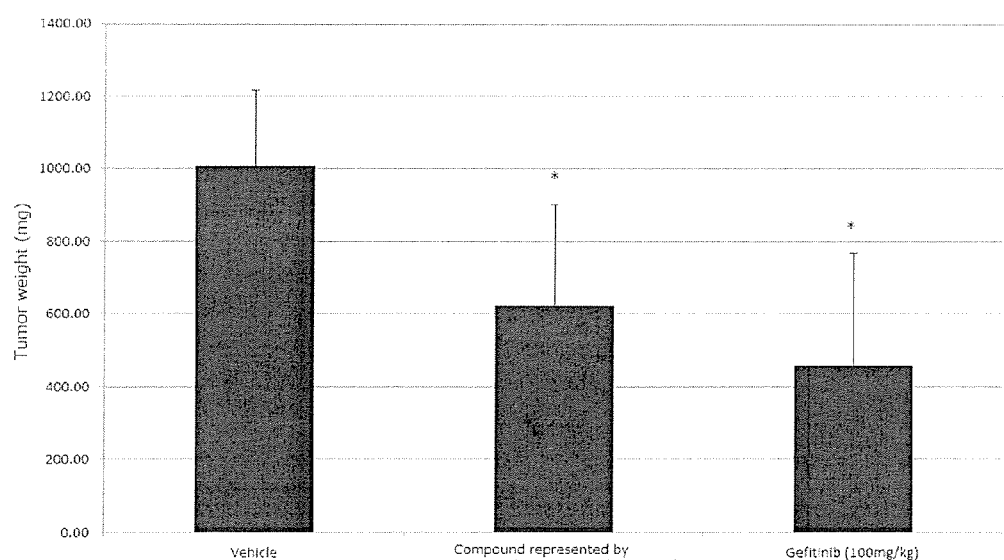
Figures 3, 5:
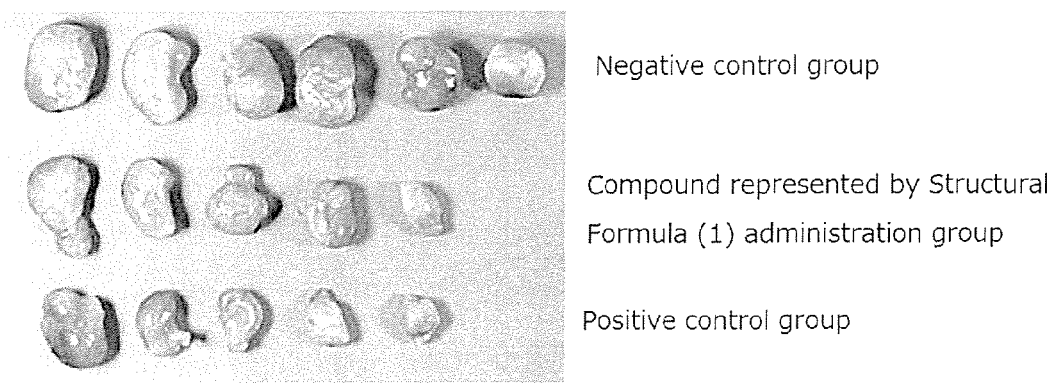
Figures 4, 5:
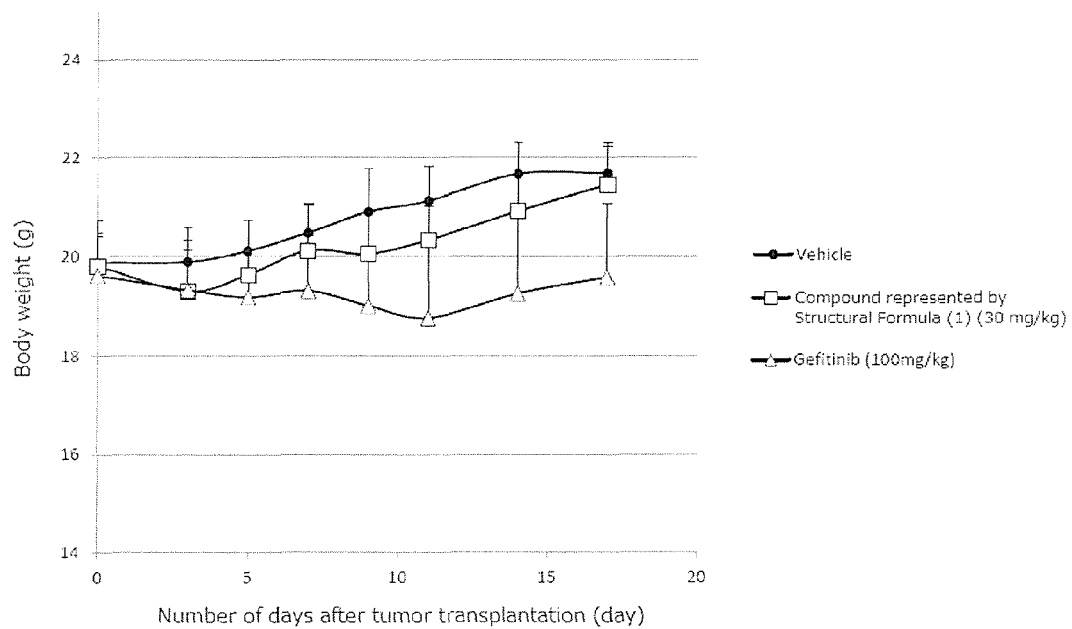

In FIGS. 5-1 to 5-4, "s (black circle)" represents the results of the negative control group, "□ (white square)" represents the results of the compound represented by the Structural Formula (1) administration group, and "Δ (white up-pointing triangle)" represents the results of the positive control group.

In FIG. 5-2, the results of the negative control group, the compound represented by the Structural Formula (1) administration group, and the positive control group are presented from the left. Note that, "*" denotes t<0.05. The inhibition rates (inhibition rates of increase in tumor weight) (%) in FIG. 5-2 are calculated assuming that the inhibition rate of the negative control group is 0%.

In FIG. 5-3, the upper row represents the results of the negative control group, the middle row represents the results of the compound represented by the Structural Formula (1) administration group, and the lower row represents the results of the positive control group.

It was found from the results in FIG. 5-1 that the NIH3T3/EGFR vIII cells exhibited significant tumorigenicity after the transplantation ((Vehicle) in FIG. 5-1).

For the results of FIGS. 5-1 to 5-3, the compound represented by the Structural Formula (1) exhibited the tumor proliferation inhibiting activity. Gefitinib also exhibited the tumor proliferation inhibiting activity. The tumor weights in the compound represented by the Structural Formula (1) administration group and the positive control group were significantly different from that of the negative control group (t<0.05). The compound represented by the Structural Formula (1) had the tumor proliferation inhibiting activity comparable to that of the Gefitinib.

Meanwhile, for the results of FIG. 5-4, weight loss was not observed in the compound represented by the Structural Formula (1) administration group and therefore the compound represented by the Structural Formula (1) was found to have no toxicity.

Test Example 5-2: NIH3T3/EGFRWT Cell-Transplanted Tumor

The NIH3T3/EGFRWT cells were prepared to 1× 10$^8$ cells/100 μL with 62.5% by volume of MATRIGEL (available from Becton, Dickinson and Company) including a DMEM medium. The resultant preparation was transplanted under the skin of 7 week-old Balb/c Nude mice.

The compound represented by the Structural Formula (1) was intraperitoneally administered repetitively once every day from 1 day to day 17 after the transplantation. The compound represented by the Structural Formula (1) was dissolved in physiological saline including 10% by mass of DMSO and 1% by mass of TWEEN80 and administered at a single dose of 30 mg/kg.

As a negative control (Vehicle), the physiological saline including 10% by mass of DMSO and 1% by mass of TWEEN80 was intraperitoneally administered once a day from 1 day to day 17 after the transplantation.

As a positive control, Gefitinib, which was an EGFR kinase inhibitor and an existing cancer therapeutic drug, was orally administered once a day from 1 day to day 17 after the transplantation. The Gefitinib was administered at a single dose of 200 mg/kg.

Note that, the negative control group included 5 animals per group, the compound represented by the Structural Formula (1) administration group included 4 animals per group, and the positive control group included 3 animals per group.

<Evaluation>

The compound represented by the Structural Formula (1) was evaluated for the tumor inhibiting effect by observing proliferation of the tumors after the cell transplantation.

—Tumor Volume—

The tumor volumes were measured in the same manner as in Test Example 5-1 and an average and a standard error thereof were determined. The results are presented in FIG. 6-1.

—Tumor Weight—

The tumor weights were measured in the same manner as in Test Example 5-1, except that the tumors were removed from the mice 18 days after the cell transplantation instead of 17 days after the cell transplantation, and an average and a standard error thereof were determined. The results are presented in FIG. 6-2. The photograph of the removed tumors is presented in FIG. 6-3.

—Change in Weight—

The mouse body weights were measured in the same manner as in Test Example 5-1 and an average and a standard error thereof were determined. The results are presented in FIG. 6-4.

Figures 1, 6:
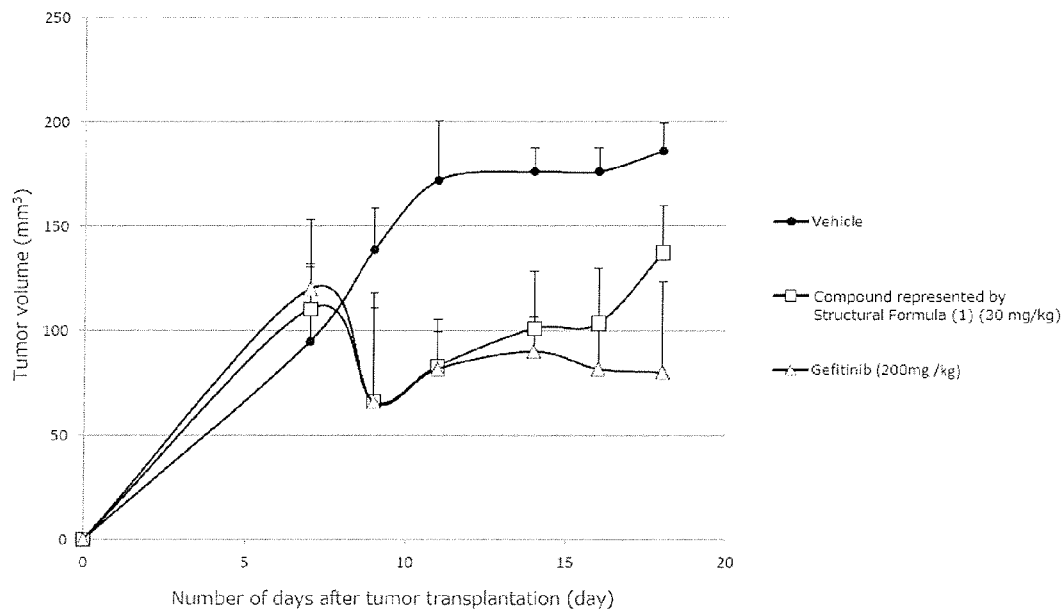
Figures 2, 6:
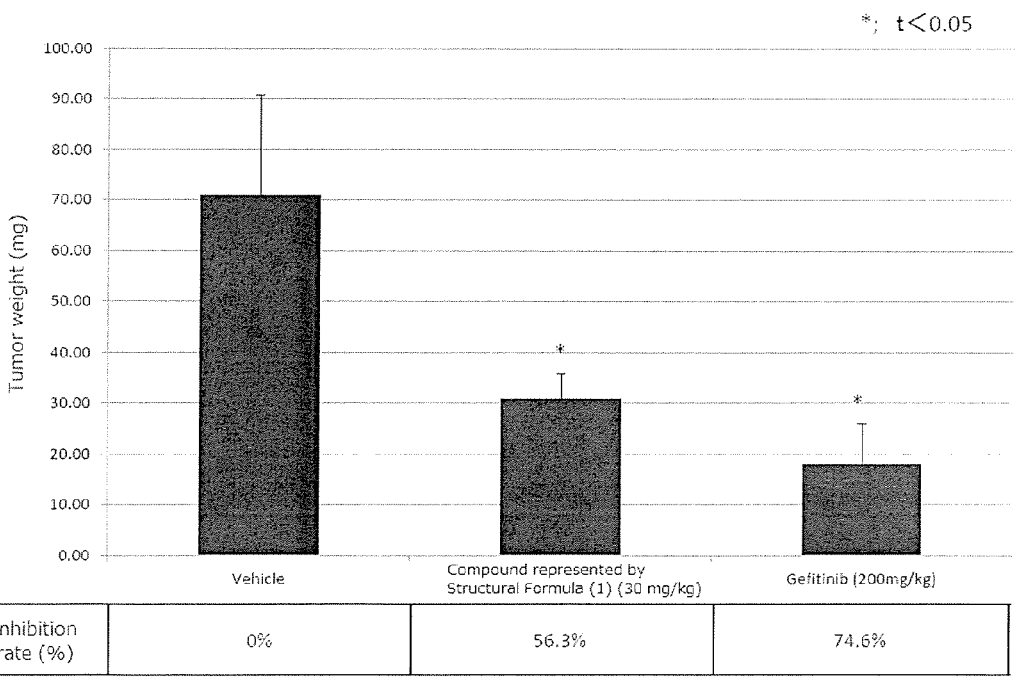
Figures 3, 6:
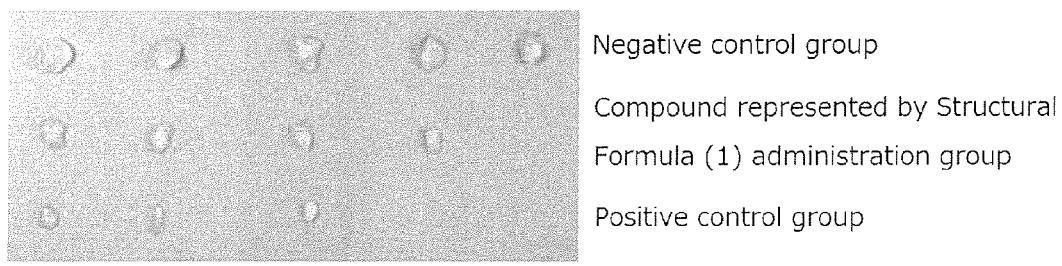
Figures 4, 6:
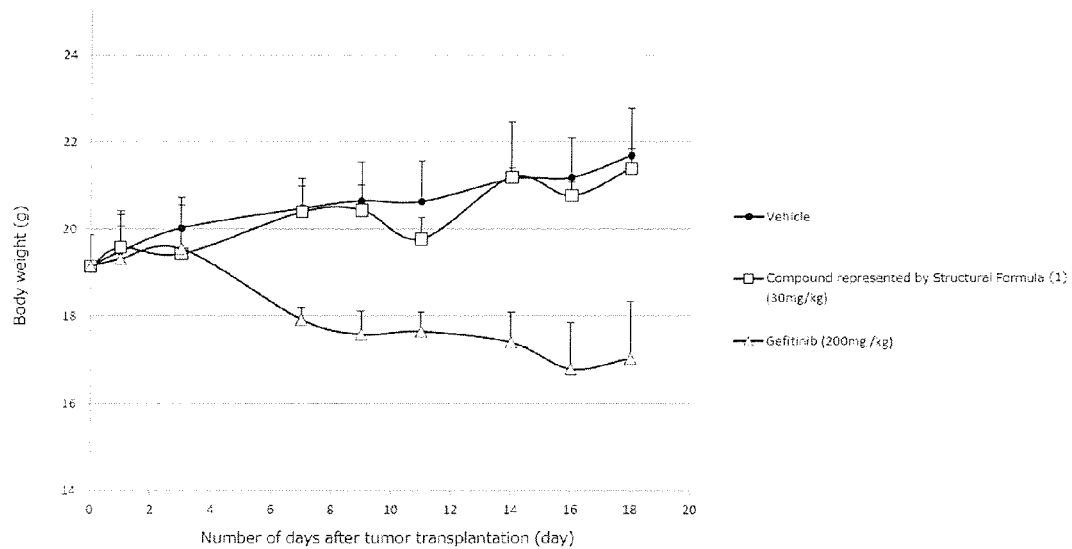

In FIGS. 6-1 to 6-4, "● (black circle)" represents the results of the negative control group, "□ (white square)" represents the results of the compound represented by the Structural Formula (1) administration group, and "Δ (white up-pointing triangle)" represents the results of the positive control group.

In FIG. 6-2, the results of the negative control group, the compound represented by the Structural Formula (1) administration group, and the positive control group are presented from the left. Note that, "*" denotes t<0.05. The inhibition rates (inhibition rates of increase in tumor weight) (%) in FIG. 6-2 are calculated assuming that the inhibition rate of the negative control group is 0%.

In FIG. 6-3, the upper row represents the results of the negative control group, the middle row represents the results of the compound represented by the Structural Formula (1) administration group, and the lower row represents the results of the positive control group.

It was found from the results in FIG. 6-1 that the NIH3T3/EGFRWT cells exhibited weak tumorigenicity after the transplantation ((Vehicle) in FIG. 6-1).

For the results of FIGS. 6-1 to 6-3, the compound represented by the Structural Formula (1) exhibited the tumor proliferation inhibiting activity. Gefitinib also exhibited the tumor proliferation inhibiting activity. The tumor weights in the compound represented by the Structural Formula (1) administration group and the positive control group were significantly different from that of the negative control group (t<0.05). The compound represented by the Structural Formula (1) had the tumor proliferation inhibiting activity comparable to that of the Gefitinib.

Meanwhile, for the results of FIG. 6-4, weight loss was not observed in the compound represented by the Structural Formula (1) administration group and therefore the compound represented by the Structural Formula (1) was found to have no toxicity. In the positive control group, weight loss was observed due to administration of Gefitinib and the Gefitinib was found to have toxicity.

It was found from the results of the Test Example 5 that the compound selected by the screening method of the present invention inhibited proliferation of not only a tumor having cancer cells expressing an epidermal growth factor receptor mutant vIII, but also a tumor having cancer cells overexpressing a wild-type epidermal growth factor receptor.

Test Example 6: Acute Toxicity Test

Test Example 6-1: Intraperitoneal Administration

The acute toxicity test was performed in the same manner as in the Test Example 4-1, except that the compound represented by the Structural Formula (1) was changed to the compound represented by the Structural Formula (8). The results are presented in FIG. 7-1.

Figures 1, 7:
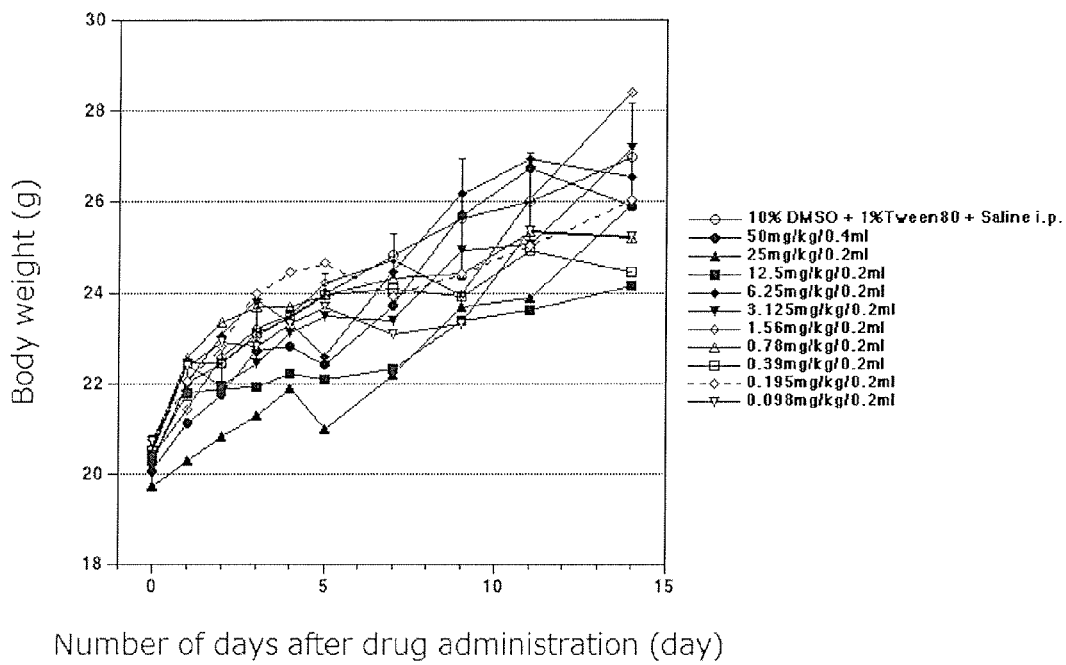
Figures 2, 7:
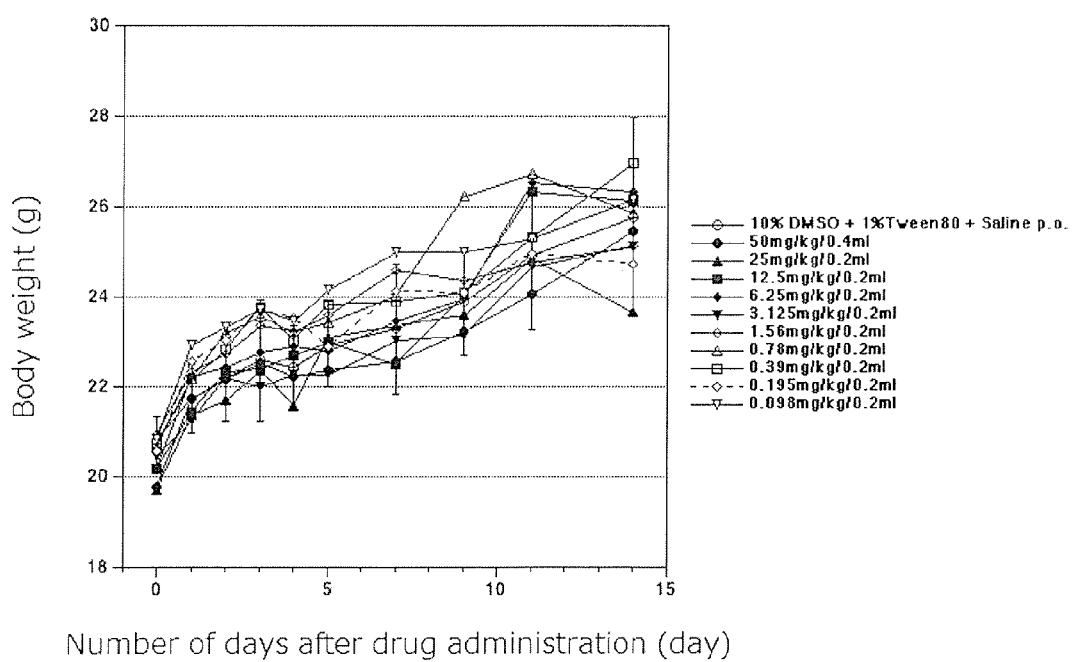

In FIG. 7-1, "● (black circle), solid line" represents the results when the compound represented by the Structural Formula (8) was administered at 50 mg/kg/0.4 mL, "▲ (black up-pointing triangle), solid line" represents the results when the compound represented by the Structural Formula (8) was administered at 25 mg/kg/0.2 mL, "■ (black square), solid line" represents the results when the compound represented by the Structural Formula (8) was administered at 12.5 mg/kg/0.2 mL, "◆ (black diamond), solid line" represents the results when the compound represented by the Structural Formula (8) was administered at 6.25 mg/kg/0.2 mL, "▼ (black down-pointing triangle), solid line" represents the results when the compound represented by the Structural Formula (8) was administered at 3.125 mg/kg/0.2 mL, "◇ (white diamond), dashed line" represents the results when the compound represented by the Structural Formula (8) was administered at 1.56 mg/kg/0.2 mL, "Δ (white up-pointing triangle), dashed line" represents the results when the compound represented by the Structural Formula (8) was administered at 0.78 mg/kg/0.2 mL, "□ (white square), dashed line" represents the results when the compound represented by the Structural Formula (8) was administered at 0.39 mg/kg/0.2 mL, "◇ (white diamond), solid line" represents the results when the compound represented by the Structural Formula (8) was administered at 0.195 mg/kg/0.2 mL, and "∇ (white down-pointing triangle), solid line" represents the results when the compound represented by the Structural Formula (8) was administered at 0.098 mg/kg/0.2 mL. Note that, "○ (white circle), solid line" represents the results when the physiological saline including 10% by mass of DMSO and 1% by mass of TWEEN80 was intraperitoneally administered.

Two-weeks after the compounds represented by the Structural Formula (8) at the above concentrations were intraperitoneally administered, the mice were dissected and organs thereof were weighed. The results are presented in Table 3-1.

TABLE 3-1

| | | Organ weight (mg) | | | | | | |
|---|---|---|---|---|---|---|---|---|
| | | Thymus | Heart | Lung | Liver | Spleen | Kidney (Right) | Kidney (Left) |
| A | Mean | 56.7 | 116.0 | 172.7 | 1679.3 | 114.0 | 179.0 | 173.7 |
| | S.D. | 12.0 | 8.7 | 12.1 | 268.1 | 14.8 | 18.7 | 18.2 |
| 50 mg/kg/0.4 mL | | 66.0 | 120.0 | 166.0 | 1551.0 | 98.0 | 152.0 | 150.0 |
| 25 mg/kg/0.2 mL | | 103.0 | 108.0 | 155.0 | 1564.0 | 138.0 | 155.0 | 149.0 |
| 12.5 mg/kg/0.2 mL | | 78.0 | 108.0 | 165.0 | 1356.0 | 111.0 | 149.0 | 150.0 |
| 6.25 mg/kg/0.2 mL | | 53.0 | 120.0 | 168.0 | 1641.0 | 124.0 | 178.0 | 158.0 |
| 3.125 mg/kg/0.2 mL | | 60.0 | 120.0 | 165.0 | 1710.0 | 132.0 | 175.0 | 172.0 |
| 1.56 mg/kg/0.2 mL | | 94.0 | 125.0 | 183.0 | 1738.0 | 158.0 | 179.0 | 161.0 |
| 0.78 mg/kg/0.2 mL | | 60.0 | 110.0 | 163.0 | 1324.0 | 127.0 | 181.0 | 177.0 |
| 0.39 mg/kg/0.2 mL | | 47.0 | 108.0 | 151.0 | 1234.0 | 69.0 | 158.0 | 146.0 |
| 0.195 mg/kg/0.2 mL | | 66.0 | 106.0 | 166.0 | 1442.0 | 98.0 | 181.0 | 174.0 |
| 0.098 mg/kg/0.2 mL | | 59.0 | 118.0 | 165.0 | 1476.0 | 176.0 | 172.0 | 160.0 |

In Table 3-1, A represents the results when the physiological saline including 10% by mass of DMSO and 1% by mass of TWEEN80 was administered.

For the results of the Test Example 6-1, no abnormalities were found at any doses. Note that, no abnormalities were found in any autopsy findings, except that slightly lighter livers, and slightly lighter or heavier spleens were found at some doses.

Test Example 6-2: Oral Administration

The acute toxicity test was performed in the same manner as in the Test Example 4-2, except that the compound represented by the Structural Formula (1) was changed to the compound represented by the Structural Formula (8). The results are presented in FIG. 7-2.

In FIG. 7-2, "● (black circle), solid line" represents the results when the compound represented by the Structural Formula (8) was administered at 50 mg/kg/0.4 mL, "▲ (black up-pointing triangle), solid line" represents the results when the compound represented by the Structural Formula (8) was administered at 25 mg/kg/0.2 mL, "■ (black square), solid line" represents the results when the compound represented by the Structural Formula (8) was administered at 12.5 mg/kg/0.2 mL, "♦ (black diamond), solid line" represents the results when the compound represented by the Structural Formula (8) was administered at 6.25 mg/kg/0.2 mL, "▼ (black down-pointing triangle), solid line" represents the results when the compound represented by the Structural Formula (8) was administered at 3.125 mg/kg/0.2 mL, "◇ (white diamond), dashed line" represents the results when the compound represented by the Structural Formula (8) was administered at 1.56 mg/kg/0.2 mL, "△ (white up-pointing triangle), dashed line" represents the results when the compound represented by the Structural Formula (8) was administered at 0.78 mg/kg/0.2 mL, "□ (white square), dashed line" represents the results when the compound represented by the Structural Formula (8) was administered at 0.39 mg/kg/0.2 mL, "◇ (white diamond), solid line" represents the results when the compound represented by the Structural Formula (8) was administered at 0.195 mg/kg/0.2 mL, and "▽ (white down-pointing triangle), solid line" represents the results when the compound represented by the Structural Formula (8) was administered at 0.098 mg/kg/0.2 mL. Note that, "○ (white circle), solid line" represents the results when the physiological saline including 10% by mass of DMSO and 1% by mass of TWEEN80 was orally administered.

Two-weeks after the compounds represented by the Structural Formula (8) at the above concentrations were orally administered, the mice were dissected and organs thereof were weighed. The results are presented in Table 3-2.

TABLE 3-2

| | | Organ weight (mg) | | | | | | |
|---|---|---|---|---|---|---|---|---|
| | | Thymus | Heart | Lung | Liver | Spleen | Kidney (Right) | Kidney (Left) |
| A | Mean | 62.3 | 114.0 | 171.3 | 1499.3 | 122.3 | 167.0 | 155.0 |
| | S.D. | 14.2 | 11.1 | 22.2 | 228.3 | 27.6 | 3.0 | 4.4 |
| 50 mg/kg/0.4 mL | | 87.0 | 116.0 | 176.0 | 1331.0 | 133.0 | 175.0 | 158.0 |
| 25 mg/kg/0.2 mL | | 39.0 | 110.0 | 163.0 | 1184.0 | 92.0 | 152.0 | 140.0 |
| 12.5 mg/kg/0.2 mL | | 90.0 | 111.0 | 159.0 | 1375.0 | 168.0 | 167.0 | 150.0 |
| 6.25 mg/kg/0.2 mL | | 74.0 | 119.0 | 171.0 | 1342.0 | 98.0 | 183.0 | 170.0 |
| 3.125 mg/kg/0.2 mL | | 100.0 | 105.0 | 161.0 | 1241.0 | 122.0 | 156.0 | 151.0 |
| 1.56 mg/kg/0.2 mL | | 51.0 | 121.0 | 170.0 | 1371.0 | 103.0 | 152.0 | 151.0 |
| 0.78 mg/kg/0.2 mL | | 82.0 | 117.0 | 183.0 | 1371.0 | 102.0 | 171.0 | 166.0 |
| 0.39 mg/kg/0.2 mL | | 88.0 | 135.0 | 182.0 | 1524.0 | 142.0 | 185.0 | 180.0 |
| 0.195 mg/kg/0.2 mL | | 104.0 | 100.0 | 161.0 | 1191.0 | 108.0 | 146.0 | 148.0 |
| 0.098 mg/kg/0.2 mL | | 88.0 | 124.0 | 182.0 | 1322.0 | 125.0 | 181.0 | 165.0 |

In Table 3-2, A represents the results when the physiological saline including 10% by mass of DMSO and 1% by mass of TWEEN80 was administered.

For the results of the Test Example 6-2, no abnormalities were found at any doses. Note that, no abnormalities were found in any autopsy findings, except that slightly lighter livers and slightly heavier spleens were found at some doses.

Test Example 7: Anti-Tumor Effect

<NIH3T3/EGFR vIII Cell-Transplanted Tumor>

The NIH3T3/EGFR vIII cells were prepared to $1\times10^5$ cells/100 μL with 62.5% by volume of MATRIGEL (available from Becton, Dickinson and Company) including a DMEM medium. The resultant preparation was transplanted under the skin of 8 week-old Balb/c Nude mice.

The compound represented by the Structural Formula (8) was intraperitoneally administered once a day from 1 day to day 17 after the transplantation. The compound represented by the Structural Formula (8) was dissolved in physiological saline including 10% by mass of DMSO and 1% by mass of TWEEN80 and administered at a single dose of 30 mg/kg.

As a negative control (Vehicle), the physiological saline including 10% by mass of DMSO and 1% by mass of TWEEN80 was intraperitoneally administered once a day from 1 day to day 17 after the transplantation.

As a positive control, Gefitinib, which was an EGFR kinase inhibitor and an existing cancer therapeutic drug, was orally administered once a day from 1 day to day 17 after the transplantation. The Gefitinib was administered at a single dose of 100 mg/kg.

Note that, the negative control group included 8 animals per group, the compound represented by the Structural Formula (8) administration group included 5 animals per group, and the positive control group included 5 animals per group.

<Evaluation>

The compound represented by the Structural Formula (8) was evaluated for the tumor inhibiting effect by observing proliferation of the tumors after the cell transplantation.

—Tumor Weight—

Seventeen days after the cell transplantation, the tumors were removed from the mice. The tumors were weighed and an average and a standard error thereof were calculated. The results are presented in FIG. 8-1.

—Change in Weight—

The mice were weighed after the cell transplantation and an average and a standard error of thereof were calculated. The results are presented in FIG. 8-2.

Figures 1, 8:
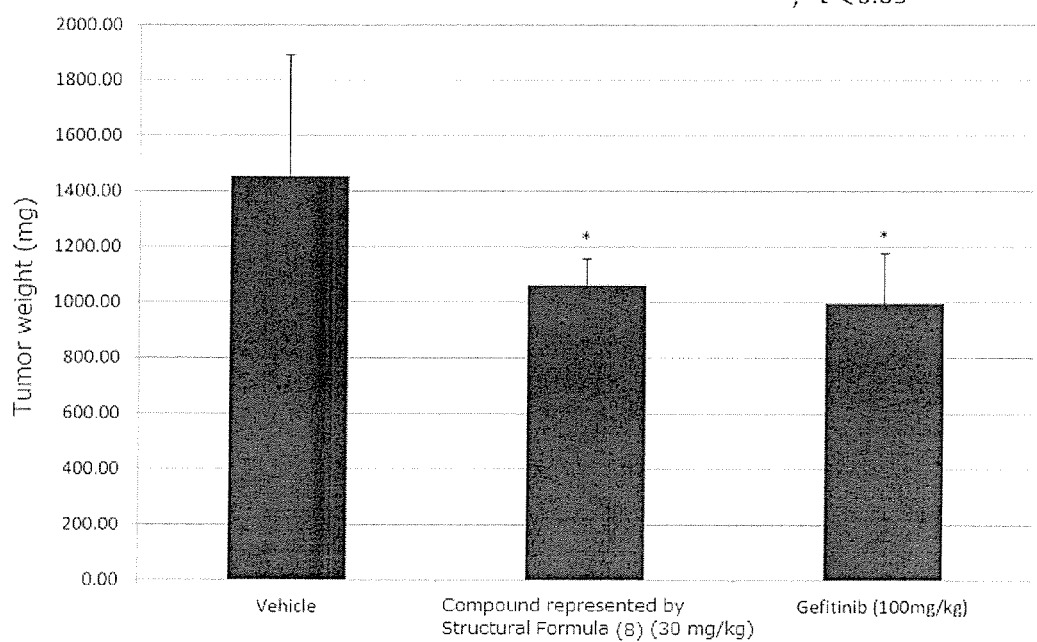
Figures 2, 8:
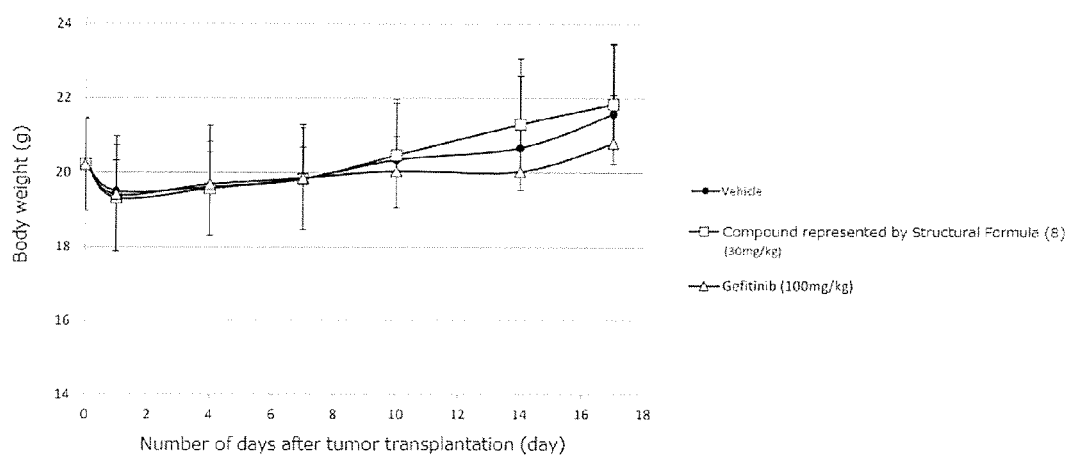

In FIG. 8-1, the results of the negative control group, the compound represented by the Structural Formula (8) administration group, and the positive control group are presented from the left. Note that, "*" denotes t<0.05. The inhibition rates (inhibition rates of increase in tumor weight) (%) in FIG. 8-1 are calculated assuming that the inhibition rate of the negative control group is 0%.

In FIG. 8-2, "● (black circle)" represents the results of the negative control group, "□ (white square)" represents the results of the compound represented by the Structural Formula (8) administration group, and "Δ (white up-pointing triangle)" represents the results of the positive control group.

For the results of FIG. 8-1, the compound represented by the Structural Formula (8) exhibited the tumor proliferation inhibiting activity. The tumor weights in the compound represented by the Structural Formula (8) administration group and the positive control group were significantly different from that of the negative control group (t<0.05).

The compound represented by the Structural Formula (8) administration group had the tumor proliferation inhibiting activity comparable to that of Gefitinib.

Meanwhile, for the results of FIG. 8-2, weight loss was not observed in the compound represented by the Structural Formula (8) administration group and therefore the compound represented by the Structural Formula (8) was found to have no toxicity.

It was also demonstrated from the results of the Test Example 7 that the compound selected by the screening method of the present invention inhibited proliferation of a tumor having cancer cells expressing an epidermal growth factor receptor mutant vIII.

Aspects of the present invention are, for example, as follows.

<1> A cancer cell proliferation inhibitor including
at least one selected from compounds represented by Structural Formulae (1) to (8) below,
wherein the cancer cell is at least one of a cancer cell overexpressing a wild-type epidermal growth factor receptor and a cancer cell expressing an epidermal growth factor receptor mutant vIII:

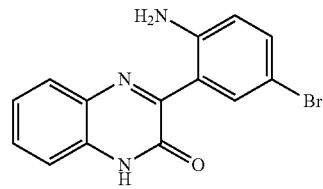

Structural Formula (1)

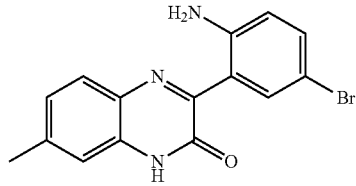

Structural Formula (2)

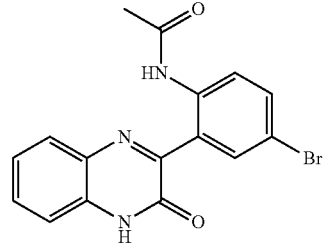

Structural Formula (3)

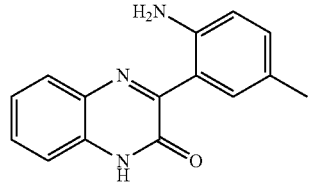

Structural Formula (4)

-continued

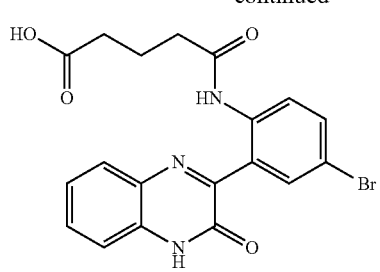
Structural Formula (5)

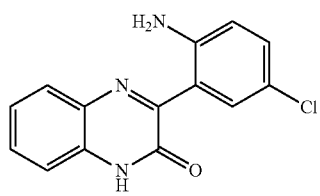
Structural Formula (6)

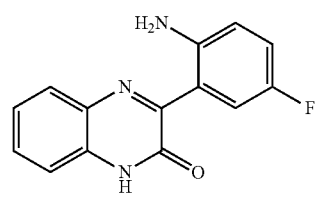
Structural Formula (7)

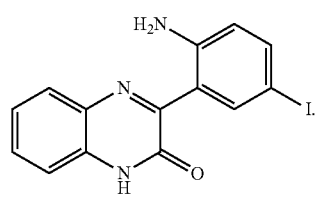
Structural Formula (8)

<2> The cancer cell proliferation inhibitor according to <1>, wherein the cancer cell proliferation inhibitor includes at least one selected from the compounds represented by Structural Formulae (1), (6), and (8).

<3> An anti-cancer agent including
the cancer cell proliferation inhibitor according to <1> or <2>.

<4> The anti-cancer agent according to <3>, wherein the cancer is glioblastoma.

<5> A method for screening at least one of a cancer cell proliferation inhibitor and an anti-cancer agent, the method including:
culturing a NIH3T3 cell expressing an epidermal growth factor receptor mutant vIII in a medium including a test substance under an environment without an adhesion scaffold;
culturing a NIH3T3 cell in a medium including the test substance under an environment with an adhesion scaffold; and
evaluating the test substance as having an activity as at least one of the cancer cell proliferation inhibitor and the anti-cancer agent when the test substance does not inhibit proliferation of the NIH3T3 cell, but inhibits proliferation of the NIH3T3 cell expressing an epidermal growth factor receptor mutant vIII.

<6> A method for preventing or treating cancer, the method including
administering the anti-cancer agent according to <3> or <4> to an individual.

<7> A compound represented by Structural Formula (8) below:

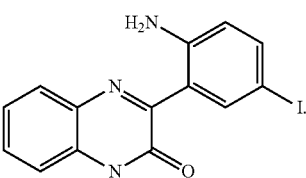
Structural Formula (8)

<8> A compound-including composition including the compound according to <7>.

The invention claimed is:
1. A cancer cell proliferation inhibitor comprising
a compound represented by Structural Formula (8) below,
wherein the cancer cell is at least one of a cancer cell overexpressing a wild-type epidermal growth factor receptor and a cancer cell expressing an epidermal growth factor receptor mutant vIII:

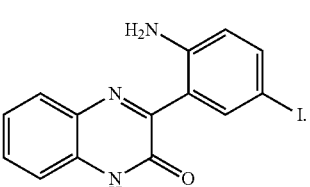
Structural Formula (8)

2. An anti-cancer agent comprising
a cancer cell proliferation inhibitor comprising:
a compound represented by Structural Formula (8) below,
wherein the cancer cell proliferation inhibitor inhibits proliferation of at least one of a cancer cell overexpressing a wild-type epidermal growth factor receptor and a cancer cell expressing an epidermal growth factor receptor mutant vIII:

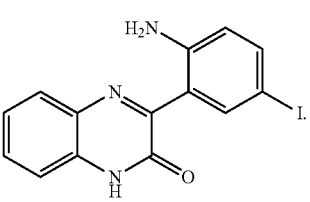
Structural Formula (8)

3. The anti-cancer agent according to claim 2, wherein the cancer is glioblastoma.

4. A method for screening at least one of a cancer cell proliferation inhibitor and an anti-cancer agent, the method comprising:
culturing a NIH3T3 cell expressing an epidermal growth factor receptor mutant viii in a medium including a test substance under an environment without an adhesion scaffold;
culturing a NIH3T3 cell in a medium including the test substance under an environment with an adhesion scaffold; and
evaluating the test substance as having an activity as at least one of the cancer cell proliferation inhibitor and the anti-cancer agent when the test substance does not inhibit proliferation of the NIH3T3 cell, but inhibits proliferation of the NIH3T3 cell expressing an epidermal growth factor receptor mutant vIII.

5. A compound represented by Structural Formula (8) below:

Structural Formula (8)

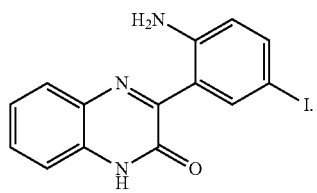

6. A compound-including composition comprising a compound represented by Structural Formula (8) below, Structural Formula (8)

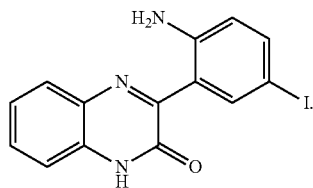

7. A method for inhibiting proliferation of a cancer cell, the method comprising:
using at least one selected from compounds represented by Structural Formulae (1) to (8) below,
wherein the cancer cell is at least one of a cancer cell overexpressing a wild-type epidermal growth factor receptor and a cancer cell expressing an epidermal growth factor receptor mutant vIII:

Structural Formula (1)

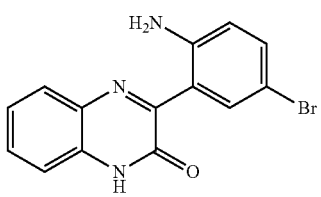

Structural Formula (2)

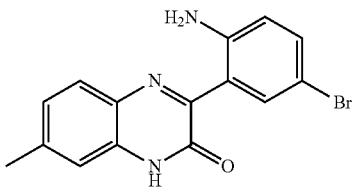

Structural Formula (3)

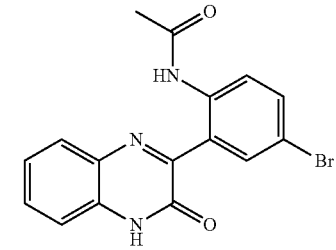

Structural Formula (4)

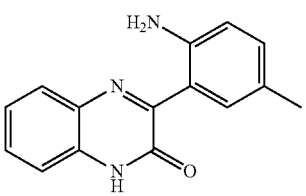

Structural Formula (5)

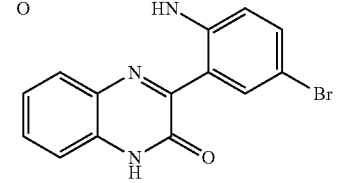

Structural Formula (6)

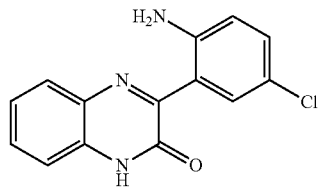

Structural Formula (7)

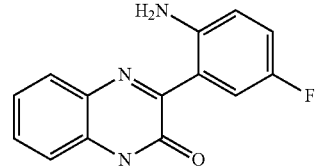

Structural Formula (8)

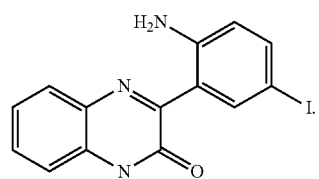

8. The method for inhibiting proliferation of a cancer cell according to claim 7, wherein the method uses at least one selected from the compounds represented by Structural Formulae (1), (6), and (8).

9. A method for treating glioblastoma, the method comprising:
administering, to an individual, an anti-cancer agent comprising at least one selected from compounds represented by Structural Formulae (1) to (8) below:

Structural Formula (1)

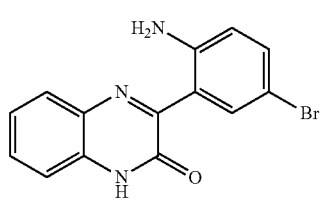

-continued
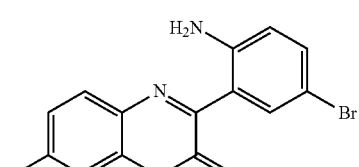
Structural Formula (2)
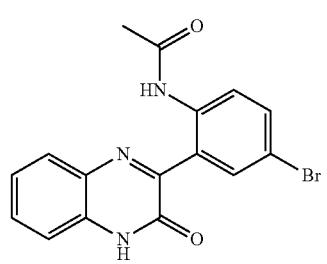
Structural Formula (3)
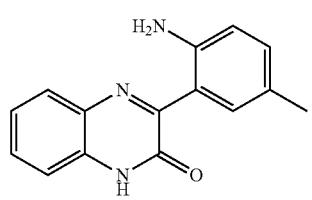
Structural Formula (4)
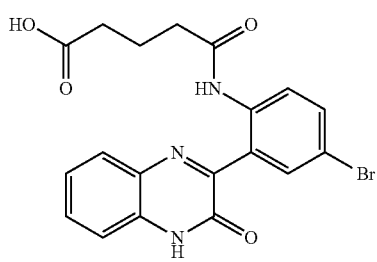
Structural Formula (5)
-continued
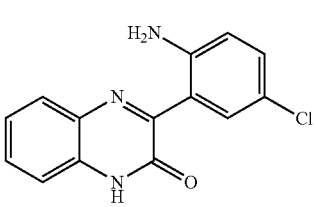
Structural Formula (6)
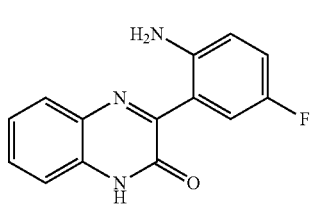
Structural Formula (7)
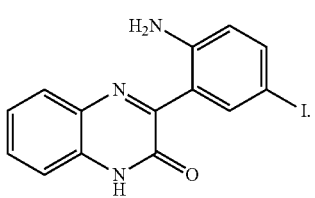
Structural Formula (8)
* * * * *